US009462945B1

(12) United States Patent
Barriga et al.

(10) Patent No.: US 9,462,945 B1
(45) Date of Patent: Oct. 11, 2016

(54) SYSTEM AND METHODS FOR AUTOMATIC PROCESSING OF DIGITAL RETINAL IMAGES IN CONJUNCTION WITH AN IMAGING DEVICE

(71) Applicant: VisionQuest Biomedical LLC, Albuquerque, NM (US)

(72) Inventors: Simon Barriga, Albuquerque, NM (US); Carla Agurto, Albuquerque, NM (US); Honggang Yu, Albuquerque, NM (US); Peter Soliz, Albuquerque, NM (US); Gilberto Zamora, Albuquerque, NM (US); Vinayak Joshi, Albuquerque, NM (US)

(73) Assignee: VISIONQUEST BIOMEDICAL LLC, Albuquerque, NM (US)

( * ) Notice: Subject to any disclaimer, the term of this patent is extended or adjusted under 35 U.S.C. 154(b) by 50 days.

(21) Appl. No.: 14/259,014

(22) Filed: Apr. 22, 2014

Related U.S. Application Data

(60) Provisional application No. 61/814,728, filed on Apr. 22, 2013.

(51) Int. Cl.
*A61B 3/14* (2006.01)
*A61B 3/00* (2006.01)
*A61B 3/15* (2006.01)

(52) U.S. Cl.
CPC ............. *A61B 3/152* (2013.01); *A61B 3/0025* (2013.01); *A61B 3/14* (2013.01)

(58) Field of Classification Search
USPC ........................................ 351/208, 206, 246
See application file for complete search history.

(56) References Cited

U.S. PATENT DOCUMENTS

| | | | |
|---|---|---|---|
| 7,290,882 B2 | 11/2007 | Collins et al. | |
| 7,338,167 B2 | 3/2008 | Zelvin et al. | |
| 7,418,123 B2 | 8/2008 | Giger et al. | |
| 7,506,982 B2 | 3/2009 | Yahagi et al. | |
| 8,132,911 B2 | 3/2012 | Smith et al. | |
| 8,150,192 B2 | 4/2012 | Niemeyer et al. | |
| 2004/0015372 A1 | 1/2004 | Bergman et al. | |
| 2004/0101181 A1 | 5/2004 | Giger et al. | |

(Continued)

OTHER PUBLICATIONS

Giger, Maryellen L. , "Computerized Analysis of Images in the Detection and Diagnosis of Breast Cancer", Semin Ultrasound CT MRI vol. 25, 2004, 411-418.

(Continued)

*Primary Examiner* — Jack Dinh
(74) *Attorney, Agent, or Firm* — Peacock Myers, P.C.; Janeen Vilven

(57) ABSTRACT

Systems and methods of obtaining and recording fundus images by minimally trained persons, which includes a camera for obtaining images of a fundus of a subject's eye, in combination with mathematical methods to assign real time image quality classification to the images obtained based upon a set of criteria. The classified images will be further processed if the classified images are of sufficient image quality for clinical interpretation by machine-coded and/or human-based methods. Such systems and methods can thus automatically determine whether the quality of a retinal image is sufficient for computer-based eye disease screening. The system integrates global histogram features, textural features, and vessel density, as well as a local non-reference perceptual sharpness metric. A partial least square (PLS) classifier is trained to distinguish low quality images from normal quality images.

26 Claims, 28 Drawing Sheets

(56) References Cited

U.S. PATENT DOCUMENTS

| | | |
|---|---|---|
| 2006/0146284 A1 | 7/2006 | Collins et al. |
| 2007/0030364 A1 | 2/2007 | Obrador et al. |
| 2007/0140538 A1 | 6/2007 | Doran et al. |
| 2007/0161876 A1 | 7/2007 | Bambot et al. |
| 2008/0100801 A1 | 5/2008 | Yahagi et al. |
| 2008/0130970 A1 | 6/2008 | Niemeyer et al. |
| 2009/0190821 A1 | 7/2009 | Marugame |
| 2009/0201467 A1 | 8/2009 | Smith et al. |
| 2009/0226065 A1 | 9/2009 | Chen |
| 2010/0054560 A1 | 3/2010 | Yamashita et al. |
| 2011/0117557 A1 | 5/2011 | Canter et al. |
| 2012/0232404 A1 | 9/2012 | Bambot et al. |
| 2012/0242817 A1 | 9/2012 | Pan |

OTHER PUBLICATIONS

Karahaliou, Anna N. et al., "Computerized Image Analysis of Mammographic Microcalcifications: Diagnosis and Prognosis", Department of Medical Physics, Faculty of Medicine, Rio, Greece, vol. 3, Issue 3, 1996, 181-190.

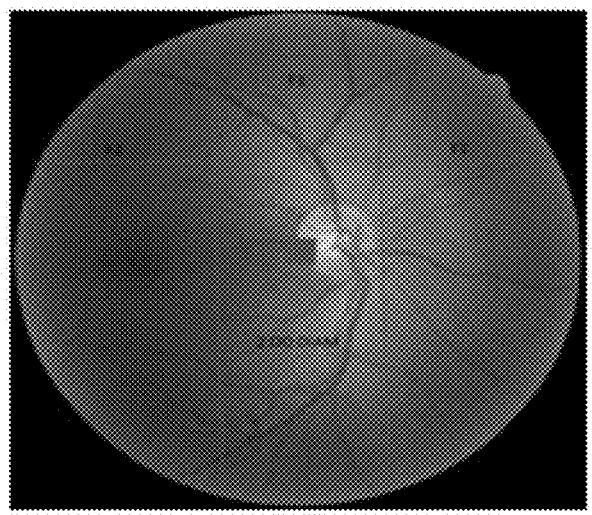
FIG. 7
 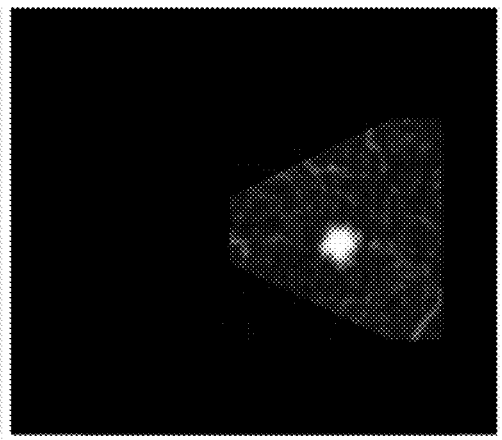
FIG. 8A  FIG. 8B

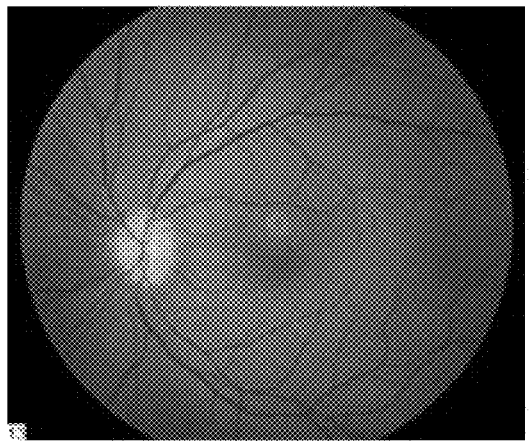
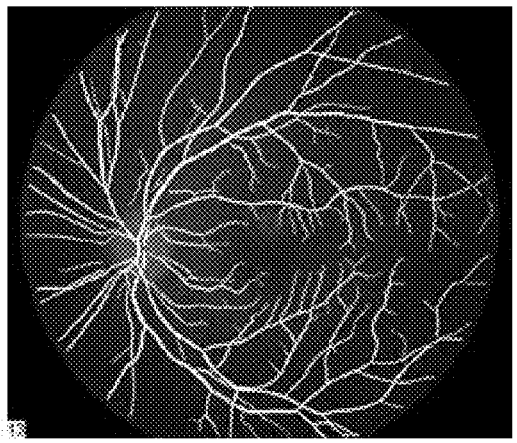
FIG. 20A    FIG. 20B
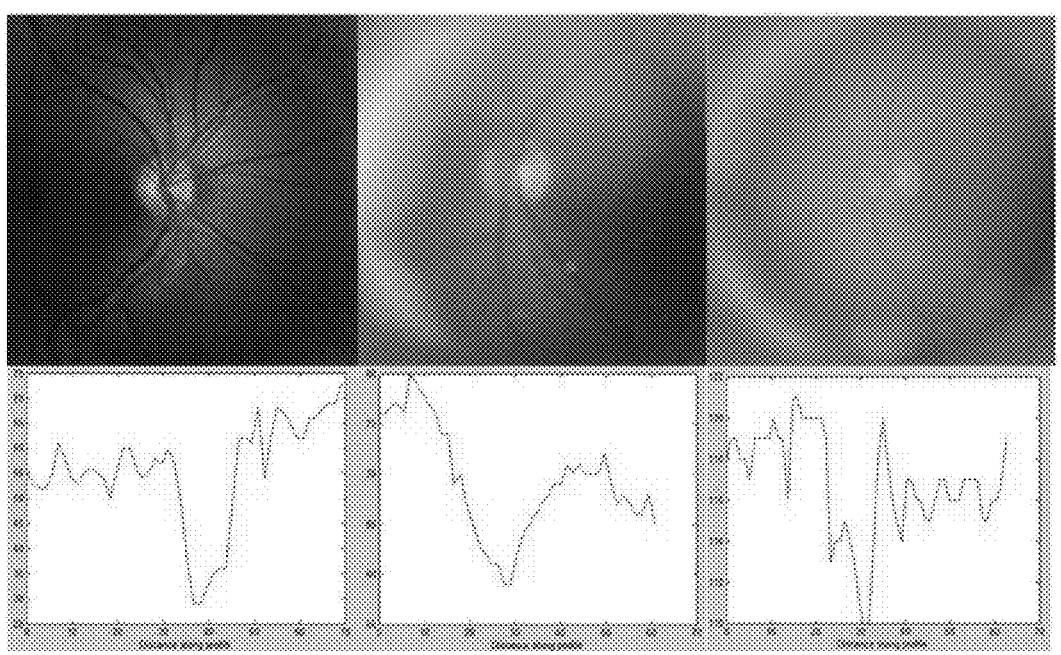
FIG. 21A    FIG. 21B    FIG. 21C

SYSTEM AND METHODS FOR AUTOMATIC PROCESSING OF DIGITAL RETINAL IMAGES IN CONJUNCTION WITH AN IMAGING DEVICE

CROSS-REFERENCE TO RELATED APPLICATIONS

This application claims priority to and the benefit of the filing of U.S. Provisional Patent Application Ser. No. 61/814,728, entitled "Automated Image Quality Evaluation of Retinal Fundus Photographs in Diabetic Retinopathy Screening", filed on Apr. 22, 2013, and is related to U.S. Pat. No. 8,515,201, entitled "System and methods of amplitude-modulation frequency-modulation (AM-FM) demodulation for image and video processing", and the specification and claims thereof are incorporated herein by reference.

STATEMENT CONCERNING FEDERALLY SPONSORED RESEARCH

This invention was made with government support under R42EY018971, R44EY018280, R43EY020015, R43EY021974, and R41EY018971 awarded by the National Institutes of Health. The government has certain rights in the invention.

FIELD OF THE INVENTION

Embodiments of the present invention relate to the integration of a method for screening images for image quality using computer implemented algorithms. More particularly one or more embodiments are directed to systems and methods of screening for image quality that are integrated into an image acquisition apparatus such as a retinal camera and are embedded into a computing unit for implementing the methods of the present invention, displaying image quality screening results to a user, and forwarding images for further processing or evaluation by a medical expert. Embodiments of the present invention are useful in a variety of contexts and applications including, for example, screening fundus images for diabetic retinopathy, screening fundus images for macular degeneration, screening of fundus images for glaucoma, screening for cardiovascular disease in fundus images, other eye disease, and telemedicine, to name a few.

BACKGROUND

Note that the following discussion may refer to a number of publications and references. Discussion of such publications herein is given for more complete background of the scientific principles and is not to be construed as an admission that such publications are prior art for patentability determination purposes.

Automatic eye disease screening by computer implemented methods is being pursued as a means to provide safe and effective screening to the more than 26 million people with diabetes in the US who need at least one screen per year and are expected to double by the year 2050. Other parts of the world such as India, Brazil, Mexico, and China share this pressing need to care for their people. However, automatic methods rely on the quality of acquired digital images to be effective and, in turn, image quality relies on photographer's ability to acquire images. Rates of unusable images in screening settings have been shown to vary from 10% to 20% depending on photographers' skills. Embodiments of the present invention relate to methods to minimize image unusable rates, e.g. 5%, and enhance the photographer's skill. Embodiments of the present invention comprise computer implemented methods for real time visual image quality feedback that can be integrated into an image acquisition apparatus as part of an eye disease screening system delivered as part of primary care.

A great effort of the research community has been directed towards the automation of computer screening systems to detect eye disease in digital fundus images. However, these systems rely on images of adequate quality in order to produce accurate results. In a DR screening system, for example, an image is deemed as inadequate when it is difficult or impossible to make a reliable clinical judgment regarding the presence or absence of DR in the image. Studies show that the percentage of images that are inadequate for screening systems is about 10% of the mydriatic (pupil dilation) images. For single field non-mydriatic (no pupil dilation) images, the percentage of inadequate quality images has been reported at 20.8%. Major causes of inadequate image quality in retinal screening images include illumination crescents due to small pupil size, loss of contrast due to poor focus or movement of the eye or media opacity, and imaging of part of the eyelid and eyelash due to blinking, as well as insufficient illumination. Inadequate images reduce the utility of automatic screening systems because they have to be discarded from analysis, or cause preventable errors in said systems.

An automatic method to assess image quality is thus a needed pre-processing step prior to an automatic eye disease screening method. Such an image quality assessment method has two main tasks. The first task is to provide visual feedback to the user as to the quality of the image, the possible source of inadequate image quality, and steps that can be taken to correct for image defects such as retaking the images while the imaging subject is still present. The second task is to assign image quality-related labels to images before forwarding for further processing or expert evaluation. These two tasks are preferably performed in real time, while the patient is still being imaged, by a computing unit that executes computer implemented algorithms and is integrated with the image acquisition system, e.g. a retinal camera.

An automatic method to assess image quality can also perform the additional task of assigning disease-related labels to images prior to further processing or expert evaluation. For example, in DR screening, the presence of advanced stages of disease is correlated to length of time a person has had diabetes. Further, image quality is also negatively correlated to subject's age, and presence and level of retinal disease. Thus, low quality images from a person can be assigned disease-related labels such as "high DR risk", or "refer".

Desktop non-mydriatic retinal cameras comprise visual aids to help the person taking the images determine whether the camera is at the correct working distance from the patient's eye and whether the retina is in focus. However, only after an image is taken does the photographer can assess the quality of the image. Besides working distance and focus, image quality factors comprise compliance with desired field of view, i.e. whether the right part of the fundus is imaged, obscuration of parts of the fundus due to alignment and illumination, which can generate crescents and shadows, debris in the optical path, smears on the camera lens, and media clarity. Taking more images after visual inspection of image quality may solve some of the problems but at the expense of time since more images are needed, the comfort of the patient since more flashes of high intensity light are needed, and, paradoxically, detriment of image quality since the patient's pupil may not reach optimum natural dilation after just a three or four images are taken. Therefore, visual aids currently available in desktop non-mydriatic cameras are insufficient to ensure efficient imaging time and quality.

The likelihood of high percentages of unusable images prevent wide adoption of retinal screening at the primary care setting and limit the clinical utility of currently available systems. Embodiments of the present invention overcome these adoption barriers and helps ensure clinical utility, thus increasing the reach of retinal screening to patients at risk who live in areas where optometry and ophthalmology have little to no reach.

Today's commercial cameras have limited clinical utility at the primary care setting because they do not ensure that rates of unusable images will be low enough to justify the investment of $25,000 or more per camera. Even low-cost camera alternatives are difficult to justify when their efficiency depends heavily on photographer skills. The present invention renders current retinal cameras clinically viable in the primary care setting. Further economic gains can be realized when the present invention is integrated into a low-cost retinal camera through an embedded computing unit as described in one of the embodiments herein.

Obtaining the highest possible image quality is critically important when photographing a patient's retina in a clinic or collecting images of a subject for a study or clinical trial. Often the photographer taking the image will not appreciate the requisite criteria for image quality required by the end user, whether an ophthalmologist or a highly trained grader or reader of the retinal images. What may appear acceptable to the photographer may be deemed unacceptable or entirely unusable by the grader. In telemedicine, transmitting an unacceptable quality image may mean, at worse a missed diagnosis, or at best the need to retake the image or images at an inconvenience to a patient who will have to return to the clinic for re-imaging. In longitudinal studies where every image is critically important, losing an image for a given examination period may result in loss of that individual from the study or a reduction in the statistical power of the results.

High-quality images are a prerequisite for automatic screening systems, such as those that employ machine-coded mathematical algorithms to determine whether images include detectable signs of disease such as diabetic retinopathy. Retinal image quality is different from image quality in other medical imaging modalities and also from recreational photography, e.g. face portraits and landscapes. In retinal imaging, image quality is related to the level of confidence that a human reader has about his/her ability to make a clinical determination of the likelihood of the presence of eye disease. Retinal image quality issues can be divided into four general areas as listed below but other will be known to those skilled in the art:

1) physics-dependent issues comprise contrast, resolution, noise, artifacts, and distortion;

2) grader- and photographer-dependent issues comprise visual perception, training, and experience;

3) task-dependent issues comprise quantitative accuracy, sensitivity, specificity, and diagnostic accuracy; and 4) patient-depended issues comprise lens and media opacities, ocular aberrations, and retinal pigmentation.

Ultimately, an automatic image quality system must consider each of these issues and provide the photographer or user with descriptive labels as to why an image may be less than optimal.

While certain types of technical errors, e.g. poor alignment, pupil centering, blinks, can be corrected by re-acquiring the retinal image, others such as camera artifacts, e.g. glares, dust, scratches on optics, etc., cannot. Some patient effects, e.g. media opacities, pupil size, poor fixation, cannot be corrected to improve image quality, but immediate feedback to the photographer can identify the cause of the problem and suggest possible avenues for mitigating the problem. These technical errors must be identified in real-time by any image quality system preferably during the alignment process and before a retinal image is acquired. This process of assessing image quality during alignment helps prevent unnecessary flash exposures to the patient whose level of discomfort may increase with each flash and whose pupils may not return to a naturally dilated stage after a few flashes of the visible light used to acquire the retinal images. Currently, there are no retinal cameras that provide real time image quality assessment during alignment or after an image is acquired. Some desktop retinal cameras provide visual aids for alignment and focus but these are not sufficient to guide the photographer to ensure maximum image quality.

In multi-site study of 2771 patients where 304 (11%) of the images were found unreadable, approximately 25% were due to poor patient fixation, 25% due to poor focus, 25% due to small pupil size or media opacity. The remaining cause(s) for unreadable images was undeterminable. The proposed image quality system will detect poor quality images that are a result of these factors, and will offer to the photographer a "help" window to correct the problem.

Depending on the application, the quality of an image is deemed deficient when it becomes difficult or impossible to make a meaningful clinical judgment regarding the presence or absence of signs of pathology in the image, as listed in Table 1. In a computerized analysis of retinal images, developers must account for images of varying quality and their impact on diagnostic results in their algorithms. For clinical studies, low quality images must be examined immediately by a photographer, a grader, or an ophthalmologist and reacquired, if needed. The development and testing of an image quality verification system based on quantitative methods that characterize image features as perceived by human users are a focus of the present invention.

TABLE 1

|  | Disc-centered image | Macula-centered image |
| --- | --- | --- |
| ACCEPTABLE | Nasal retinal vessels acceptable focus for lesion detection | Field of view or macula in soft focus but gradable |
|  | Moderate amount of shadowing/macula | Reasonable contrast |
|  | Reasonable contrast | Optic disc with gradable features |
|  | Lightning artifacts less than 10% of the whole image | Lightning artifacts less than 10% of the whole image |
|  | Confidence in lesion identification | Confidence in lesion identification |
| UNACCEPTABLE | Distinct media haziness or poor photographic focus | Field of view or macula vessels: cannot discern due to haze or shadow |
|  | More than 25% of image with artifacts leading to unreadability of area | More than 25% of image with artifacts leading to unreadability of area |
|  | Low confidence in lesion identification | Low confidence in lesion identification |

Automatic image quality assessment has been the topic of intense study by a number of researchers in other fields of medicine as well as the general topic of image quality. Reference image-based methods (i.e. a quality comparison with the optimal image of each retina is made using various quantitative measures) are disadvantageous because a limited number of the good quality images might not be a "good" reference for the natural large variance encountered in retinal images acquired from screening. Other methods include vessel detection in the whole image for image quality assessment, measurement of vessel density in a region around the macula for macula-centered images, and splitting the field of view into sub-regions with different sizes of elliptical rings and different angles, wherein the local vessel density and 5-bin color histogram features were used to determine image quality. Some methods involve segmentation of retinal vessels and other anatomical structures, then applying additional criteria, such as detecting small vessels around the fovea, to determine image quality. The practical utility of these techniques is very low because they are computationally intensive (not suited for real-time feedback to a photographer) and have an inherent uncertainty regarding a valid or successful segmentation step (such as finding small vessels to determine the quality of a retinal image).

Other methods include an image management method that assigns descriptive labels to images according to image quality factors in order to indicate to a user possible actions such as "delete", "keep", "keep and enhance". The utility of these methods is limited to "recreational" photography where the image quality factors include image brightness, contrast, and focus. In medical imaging screening methods, such as the subject matter of the present invention, said image quality factors are necessary but not sufficient to provide an indication of the adequacy of an image. These recreational photography methods fail to consider other factors involved in assessing image quality of medical images in general and retinal images in particular. In the case of retinal images there are three quality factors that are important and unique to this imaging modality.

The first one relates to the image adequacy with respect to a specific imaging protocol, for example, an imaging protocol that requires images of certain, pre-defined areas of the fundus, e.g. the macula or the optic disc. A retinal image can have adequate levels of brightness, contrast, or focus but if one of these areas is not present, the image is unusable for practical purposes. An image quality screening method thus has to include factors that include adequacy to imaging protocols and give the user the option of retaking an image.

The second factor is the assessment of artifacts that obscure parts of the images required for adequate screening. These factors are described herein as part of the present invention but briefly, they include artifacts due to human factors such as small pupils, eye blinks, and media opacities among others "physiologic image quality artifacts", that will be obvious to those skilled in the art. The assessment of physiologic image quality artifacts is unique to retinal imaging and its implementation as computer-implemented methods is unique to embodiments of the present invention.

The third factor relates to assessment of "case completion". In retinal imaging, a case is considered complete when a pre-determined minimum set of adequate images is collected. This minimum set relates to a specific imaging protocol designed to capture certain areas of the eye fundus for screening. An image quality screening method for retinal screening thus requires methods that determine when a case is complete. This image quality factor is unique to retinal screening and its implementation as machine-implemented methods is unique to the present invention. The combination of these three image quality factors is not only unique to retinal image screening but necessary for its utility in practice. Further, said combination of image quality factors has not been reported in the literature or applied in practice. As it will become clear from the description of methods herein, the present invention includes the combination of methods that implement the three image quality factors needed to make automatic retinal screening useful and practical.

Other methods do not require any segmentation of the image, such as integrating individual characteristics to give a better evaluation of image quality than the individual parts, primarily in other fields not directly related to medical applications. For example, spatial features based on wavelets have been used to show that image characteristics such as spatial frequency, noise, sharpness, brightness, contrast, and modulation transfer function could be encoded by the wavelets. These characteristics, in turn, relate to image quality. However, this technique is computationally intensive and not suitable for real-time applications. Another method uses clustering of multiscale Gaussian derivative filterbank responses to obtain a compact representation of image structures. Image Structure Clustering (ISC) provides a compact representation of the structures found in an image, and determines the most important set of structures present in a set of normal quality images, based on a clustering of the response vectors generated by a filter bank. Clustering of filter bank responses has been used for different applications in image processing. The system is based on the assumption that an image of sufficient quality will contain a definable distribution of image structures. A cluster filter bank response vector is used to represent the image structures found within an image. Using this compact representation together with raw histograms of the Red, Green, and Blue (RGB) color planes, a statistical classifier can be trained to distinguish normal from low quality images. Though effective in evaluating image quality (0.997 area under the area under the receiver operating curve, AUC), this approach was found to require up to 30 seconds to perform the necessary calculations, thus exceeding the practical limits for clinical, real-time applications.

Others methods use global image intensity histogram analysis and combinations of local and global histogram analysis to automatically assess image quality. The difference between a test image histogram and a model histogram from good quality images is used to give an image quality metric. Some studies perform an analysis of the vasculature in a circular area around the macula. The presence of small vessels in this area is used as an indicator of image quality. Some methods use computational models for evaluating the acceptability of retinal images based on several criteria related to image quality. Several steps are required, including segmenting retinal vessels. To evaluate the clarity of an image, retinal vessels in the vicinity of the fovea are counted and measured. The clear presence of these vessels indicates a high-quality image. Other factors that affect image quality are individually addressed and quantitative criteria are set for each. This technique is computationally burdensome and must integrate explicitly all possible factors, each treated independently with a different algorithm. The method requires a segmentation of the vasculature and other major anatomical structures to find the region of interest around the fovea. Detecting the failure of the segmentation in case of low image quality is not trivial and limits the robustness of the approach and its clinical utility.

SUMMARY OF THE INVENTION

According to one embodiment of the present invention a method to perform automatic retinal screening is provided wherein a retina is illuminated using an illumination source. A retinal image is captured with a retinal camera and the image is transmitted to a processor. An assessment in real time is performed via the processor of the image quality and the camera is adjusted if the image quality does not meet predetermined quality requirements. For example the performing step determines alignment of the image according to one or more imaging protocols. Further a descriptive label is assigned to the image as to its adequacy according to one or more imaging protocols. In another example the performing step determines presence and extent of crescents and shadows in the image. Further a descriptive label is assigned to the image as to the image as to presence and extent of crescents and shadows. In yet another example, the performing step determines quantitative image quality of the image via a classification process trained using examples of visual perception by human experts. Further a descriptive label is assigned to the image as to its quantitative image quality. According to another example the performing step classifies the image according to a set of image quality labels. Further a descriptive label is assigned to the image as to its image quality.

The adjusting step may employ a user interface to indicate a user quality of the image and suggested actions to take with respect to the camera.

In another embodiment the executing step performs real time analysis of likelihood of presence or absence of disease in the retina of the image. Further a label is assigned to the image indicative of the likelihood. Further still the executing step employs a decomposition phase using AM-FM methods to decompose the image into magnitude, frequency, and angle of each image pixel across a plurality of spatial scales. The executing step may additionally employ a feature extraction phase to group decomposition phase components into feature vectors. Further still the executing step may additionally employ a feature reduction phase to reduce number of features. Alternatively, the executing step additionally comprises tuning one or more parameters to vary assignment of labels and/or performance of a classification model in terms of sensitivity and specificity. For example, the executing step employs a two-tier threshold to assign labels to the image in two steps. For example, the first step comprises a high sensitivity classification model. Additionally, the second stop comprises a high specificity classification model.

In yet another embodiment, a system to perform automatic retinal screening is disclosed having an illumination source illuminating a retina; a retinal camera capturing a retinal image; a processor receiving the image, performing an assessment in real time of the image quality, and adjusting the camera if the image quality does not meet predetermined quality requirements.

In a further embodiment, a method to automatically determine image quality of a retinal image is provided. The method comprising the steps of illuminating a retina using an illumination source; capturing the retinal image with a retinal camera; transmitting the image to a processor; performing via the processor an assessment in real time of the image quality, comprising determining alignment of the image according to one or more imaging protocols; determining presence and extent of crescents and shadows in the image; and determining quantitative image quality of the image via a classification process trained using examples of visual perception by human experts; and adjusting the camera if the image quality does not meet predetermined quality requirements.

Objects, advantages, novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate an embodiment of the present invention and, together with the description, serve to explain the principles of the invention. The drawings are only for the purpose of illustrating various embodiments of the invention and are not to be construed as limiting the invention. In the drawings:

FIG. 5(a) is an image taken with the retinal camera of FIG. 3. FIG. 5(b) is an image taken with a Canon CR 1 Mark II desktop retinal camera. FIGS. 5(c) and 5(d) are details of microaneurisms. The images from both cameras show the same level of detail and are adequate for further processing or evaluation.

FIG. 6(a) is an image taken with the retinal camera of FIG. 3. FIG. 6(b) is an image taken with a Canon CR 1 Mark II desktop retinal camera. FIGS. 6(c) and 6(d) are details of pre-retinal hemorrhages. The images from both cameras show more detail on the lesions and are adequate for further processing or evaluation.

FIG. 7 depicts areas of field detection used by the Alignment step 342.

FIG. 8A illustrates a retinal image and FIG. 8B depicts an example of a probability map used by the Macula Detection step 710 to detect the macula within a retinal image shown in FIG. 8A.

FIG. 16a shows the green channel of the original fundus image; FIG. 16b is a Gaussian filtered image; FIG. 16c is a gradient-based filtered image; and FIG. 16d is a filtered gradient image to detect crescents.

FIG. 20 shows an example of retinal vascular segmentation. FIG. 20A is a retinal fundus image, and FIG. 20B is the local vessel entropy segmentation with Hessian enhancement overlaid on the original image.

FIG. 21 shows an example of local sharpness metrics of a retinal image. FIG. 21A shows an adequate quality image with sharpened edges, CPBD=0.61, EBR=0.69. FIG. 21B is an inadequate quality due to defocus, CPBD=0.26, EBR=0.34. FIG. 21C shows an inadequate quality image due to a cataract, CPBD=0.75, EBR=0.35.

DETAILED DESCRIPTION OF EMBODIMENTS OF THE INVENTION

Figure 1:
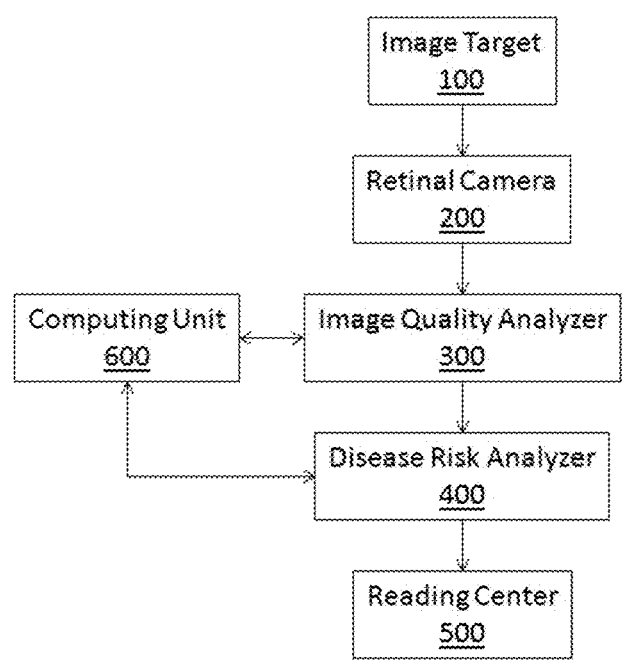
FIG. 1 illustrates a flow of images, data, and analysis for image quality and eye disease screening.

Embodiments of the present invention overcome barriers to adoption of retinal imaging at the primary care setting by the combination of a low-cost, portable, easy to use retinal camera and methods to ensure that the number of images of adequate image quality is minimized. Moreover, determination of image quality is preferably provided in real time to the person acquiring the images, i.e. the user, before image acquisition, i.e. during alignment of the camera to the patient's eye. Real time image quality preferably comprises descriptive labels that indicate potential causes of inadequate image quality and visual aids that guide the user on maximizing image quality. This principle can be extended such that an image with one or more image quality defects that is acquired under limiting factors, such as but not limited to patient's pupil size and unclear media, e.g. cataracts, should be given the opportunity to be accepted by the user. Accordingly, a classification process is preferably performed which provides the user with guidance as to keep an image of adequate quality, keep an image of inadequate quality, or to retake an image of inadequate quality. The embodiments described herein, by using real time retinal image screening, provide a level of effectiveness and efficiency not available in prior art systems.

The present invention relates to a system and methods for acquiring retinal images for automatic screening by machine-coded algorithms running on a computational unit. The present invention comprises methods that allow a user to use a retinal camera to record retinal images with adequate image quality according to certain rules that determine the quality of the images for further machine-based or human-based processing and/or clinical assessment. Image quality methods of the present invention comprise quantitative measurement of, for example, field of view, illumination and alignment artifacts, media opacities, debris in the optical path, and deviation from a standard imaging protocol. A set of thresholds on the values of these image quality features can preferably be determined so that images can preferably be assigned image quality-associated labels such as "adequate", "inadequate", "retake", and others as explained herein. Image quality methods of the present invention comprise machine-based transformations that can be carried out onboard a computing device integrated directly into a retinal camera. The present invention also relates to methods to assign labels to sets of one of more retinal images related to the likelihood of the presence of eye disease as determined by machine code.

The present invention can provide retinal screening to human patients at risk of eye disease such as diabetic retinopathy, macular degeneration, cataracts, and glaucoma. In one application of the present invention, a user uses the present invention to record images of the fundus of adequate image quality to allow further methods to assign labels to the images in relation to the likelihood of the presence of fundus disease. In one application of the present invention, further methods assign labels such as "Refer", "No Refer", or "Indeterminate" to sets of acquired fundus images. Those fundus images labeled Refer or Indeterminate can be forwarded to a reading center for visual inspection by human experts according to telemedicine methods. Other applications of the present invention will become obvious to those skilled in the art.

Embodiments of the present invention enable users to obtain and record retinal images of adequate image quality to allow further methods to execute machine-based and/or human-based clinical assessment. Fundus cameras have the shortcoming of not comprising real time feedback on image quality and therefore they are of limited clinical utility. Traditional fundus cameras may comprise visual aids of focus and working distance but these aids have the shortcoming of not providing information to the user on other image quality features comprising field of view, illumination and alignment artifacts, media opacities, debris in the optical path, and others that will become obvious to others skilled in the art. Thus the present invention fills an unmet need for a system and methods that ensures adequate quality images at the point of care, thus eliminating the need for re-scheduling and re-imaging of a patient because of inadequate quality images.

In the embodiments of the present invention described herein a retinal camera and imaging protocol are described as non-limiting examples. It will become obvious to those skilled in the art that other retinal cameras and other imaging protocols can be employed without affecting the applicability and utility of the present invention.

FIG. 1 depicts a flow chart showing phases of automatic processing of retinal images in conjunction with an imaging device in accordance with the first embodiment. Automatic processing is defined as determining the quality of the retinal images, providing feedback to a user regarding said image quality, and determining the likelihood of presence of eye disease. The retinal imaging process begins with the imaging target 100. The imaging target can take many forms including a human eye or an artificial target simulating a human eye. Other imaging targets will be known to those skilled in the art.

The next phase of the retinal imaging process is the image acquisition using a retinal camera 200. Retinal image quality is first and foremost depending on the imaging device, i.e. retinal camera 200. One or more embodiments of the present invention include methods to optimize retinal image quality using selection of alignment, focus, and imaging wavelengths. Image acquisition can take many forms including, capturing an image with a digital camera and capturing an image or a series of images as in video with a digital video camera. Retinal cameras typically employ two steps in acquiring retinal images. In the first step an alignment illumination source is used to align the retinal camera to the area of the retina that is to be imaged. In mydriatic retinal cameras this alignment illumination source can comprise a visible source, while in non-mydriatic retinal cameras a near infrared illumination source that does not affect the natural dilation of the pupil is preferably used. The second step is image acquisition, which comprises a visible illumination source driven as a flash or intense light. This flash of light is intense enough that allows the retinal camera to capture an image and short enough to avoid imaging the movements of the eye. An embodiment of the present invention is a non-mydriatic retinal camera that uses near-infrared light for the alignment illumination source and generates a live, i.e. real time, video signal of the parts of the retina to be imaged. Other methods for capturing and acquiring retinal images will be known to those skilled in the art. The retinal camera preferably can capture at least one longitudinal point in time.

The next phase of the retinal imaging process utilizes the Image Quality Analyzer 300, in which the video signal of the retina is preferably automatically analyzed according to one of more imaging protocol and image quality criteria to detect whether an image is in agreement with an imaging protocol, includes detectable image quality defects, and the extent of such agreement and defects. On the basis of this analysis the video signal and one or more visual aids are preferably shown to the photographer to guide the photographer on changes to the camera alignment that may result in improved image quality. Once a retinal image is acquired, such image is preferably automatically analyzed according to imaging protocol and/or image quality criteria to detect whether such image is in agreement with the imaging protocol, includes detectable image quality defects, and the extent of such agreement and defects. On the basis of this analysis the acquired retinal image is preferably assigned to a class indicative of its clinical utility, the extent and nature of detected image quality defects, and whether such image should be retaken.

The next phase of the retinal imaging process utilizes the Eye Disease Analyzer phase 400, in which one or more retinal images are automatically analyzed according to one or more disease risk criteria to detect whether such image or set of images include signs of presence of fundus disease. On the basis of this analysis the image or set of images are preferably assigned to a class indicative of the present of risk of disease. The set of classes may include a class corresponding to an image that cannot be analyzed due to inadequate image quality. This phase may utilize techniques and devices disclosed in U.S. Pat. No. 8,515,201.

The next phase of the retinal imaging process involves Reading Center 500, where a retinal image or a set of retinal images labeled as "Refer" as described below are visually analyzed by human experts according to one or more disease classification criteria to detect whether such image or set of images include detectable lesions and/or features and the extent of such lesions and/or features. On the basis of this analysis the image or set of images are assigned to a class indicative of the presence of disease, the extent of disease, and guidance for follow up care.

The phases comprising Image Quality Analyzer 300 and Eye Disease Analyzer phase 400 are preferably implemented by machine-coded mathematical algorithms that run on Computing Unit 600. The Computing Unit 600 preferably comprises one or more types of random-access and read-only memory, one or more types of processors, and one or more types of human interface units including but not limited to keyboard, touch screen, display, and light indicators. The Computing Unit 600 carries out one or more real time image transformations, analyzes, and classifications according to mathematical algorithms in representations outside the space and time representations understood by the human brain and at processing speeds superior to what human brains can do.

Figure 2:
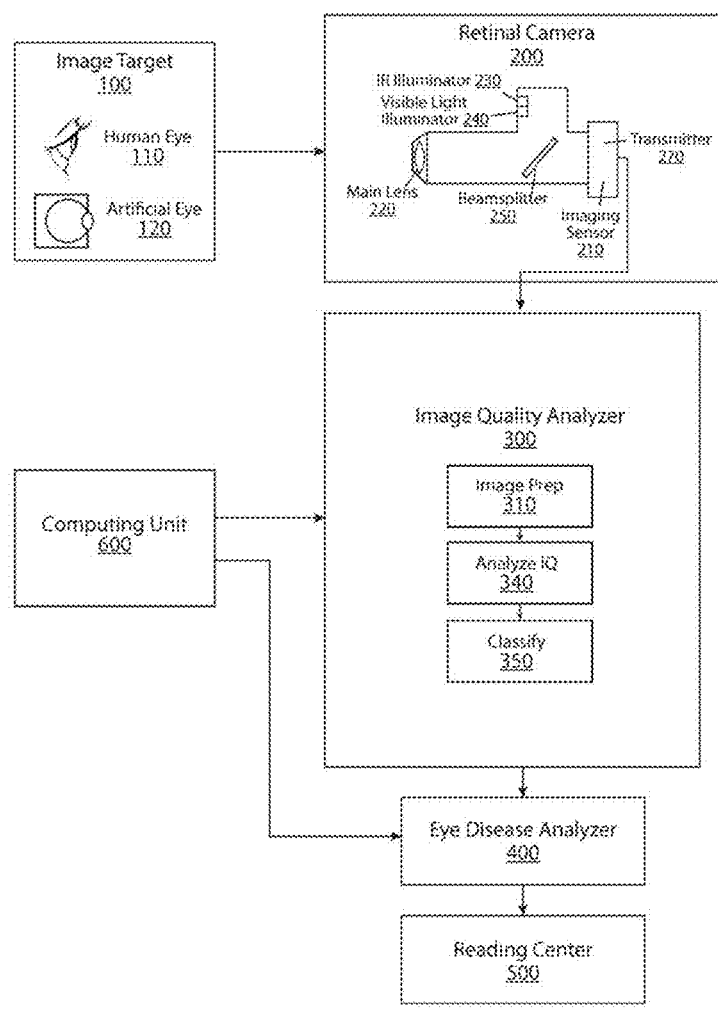
FIG. 2 depicts a more detailed view of the processes in FIG. 1.

FIG. 2 is a more detailed view of the retinal imaging process. The Image Target phase 100 comprises the object to be imaged. There are many objects that can be imaged. The preferred imaging target is a human eye 110 with a pupil size of at least 3.7 mm and clear media, e.g. no cataracts. An alternative imaging target is an artificial eye 120 comprising one or more optical apertures simulating a human pupil, an internal spherical cavity simulating the interior of the human eye, and an internal surface that can simulate the physiological features of the human retinal. The internal cavity of an artificial eye can also be made of a material with reflectivity characteristics that can be used to characterize and/or calibrate a retinal camera. Other alternative imaging targets will be known to those skilled in the art.

Retinal Camera 200 is used to obtain and record digital images of the imaging target 100. An embodiment of retinal camera 200 is an imaging sensor that can capture the light reflected from imaging target 100. In one embodiment of the present invention said imaging sensor can be a commercial camera such as a digital single lens reflex (DSLR) camera 210. The main advantage in using a commercial DSLR is that these devices comprise imaging sensors and associated hardware and firmware that simplify the imaging and acquisition of retinal images. The optical element of Retinal Camera 200 that enables imaging the fundus of the eye is main lens 220. In one embodiment of the present invention the main lens is a +28 Diopter indirect ophthalmoscopy lens which results in an effective field of view of approximately 30 degrees on the retina. In an alternative embodiment a +40

Diopter main lens results in an effective field of view of about 45 degrees on the retina. The system optionally comprises a mechanism to switch between two or more main lenses in order to change the effective field of view of the retinal camera. Other methods to use and combine other types of main lenses will be known to those skilled in the art.

In one embodiment multiple illumination sources, including a near infrared source 230 and one or more (preferably at least two) sources of visible light 240 are preferably combined by a dichroic beam splitter, i.e. a hot-mirror, in order to simplify the design and construction of the retinal camera. The illumination sources preferably comprise LEDs. The near infrared source 230 is preferably used to align the camera to the area of the fundus to be imaged without affecting the natural dilation of the subject's pupil. Once alignment is achieved, the one or more visible light sources 240 are commanded to emit a flash of light that illuminates the retina momentarily and allows the retinal camera to capture an image of the retina. The wavelength and illumination intensity of the visible sources 240 are preferably selected to optimize the contrast offered by the characteristic reflectance and absorption of the natural chromophores in the retina. In this way illumination entering the pupil is minimized while captured reflected light is maximized adding to the comfort of the subject and reducing the effect of the light on the subject's natural pupil dilation. The near infrared illumination source 230 may be mounted on a passive heat sink. The visible light illumination sources 240 may be mounted on an aluminum plate and operated in pulsed mode (20 ms-1 s). The typical high spherical aberration of main lens 210 preferably removes non-uniformity of LED illumination sources.

In one embodiment of retinal camera 200 the near infrared illumination source 230 has a central wavelength of 850 nm (CW). At this wavelength, the light penetrates the different layers of the retina up to the choroid, and alignment of the camera is done using this layer. In another embodiment of retinal camera 200 the near infrared illumination source 230 has a central wavelength of 760 nm (CW), which enables the camera to be aligned against inner layers of the retina such as the retinal vasculature. In yet another embodiment of the retinal camera the near infrared illumination source 230 can be switched between different central wavelengths, e.g. between 760 nm and 850 nm, in order to align the camera against retinal features on different layers of the retina. Other methods to illuminate the retina for alignment will be known to those skilled in the art.

In one embodiment of retinal camera 200 a white light LED can be used as the visible light illumination source 240. The color temperature of the white light LED determines the color balance in the resulting retinal image. An alternate embodiment of the retinal camera 200 comprises a method to select among two or more color temperatures of the white LED illumination source 240 in order to obtain different degrees of color balance among retinal features. For example, retinal vasculature is more prominent in the green channel whereas differences in retinal pigmentation due to melanin may call for different color temperatures in order to compensate for these differences. Yet another embodiment of the retinal camera comprises a tri-color LED illumination source 240 and a method to change the intensity of each of the three colors in order to optimize color balance in acquired retinal images. Other methods to use and combine other types of visible light illumination sources will be known to those skilled in the art.

In one embodiment of the retinal camera 200 a beamsplitter 250 is used to allow light to be directed to the retina and then captured by the image detector 210. One embodiment of the retinal camera 200 uses a nano-wire polarizer beamsplitter 250. A nano-wire polarizer beamsplitter combines two roles in one single device: a beamsplitter to allow light to be directed to the retina and then captured back at the image detector and a polarizer to minimize back reflections from other optical components and the eye's cornea as well as permitting using a small central obscuration. The use of a nano-wire polarizer beamsplitter makes the retinal camera 200 easier and cheaper to manufacture and calibrate compared to other devices that use separate components for beam splitting and polarization.

The retinal camera 200 preferably further comprises an electronic transmission system to transmit images or video feed 270 of the areas of the retinal illuminated by the near infrared illumination source 230 and the visible illumination sources 240 to the next phase of the Retinal Imaging Process. Example systems can include wired transmission according to the HDMI standard, wireless transmission according to the Wi-Fi standard, and solid state memory media such as Secure Digital cards. Other transmission methods will be known to those skilled in the art.

Figure 4:
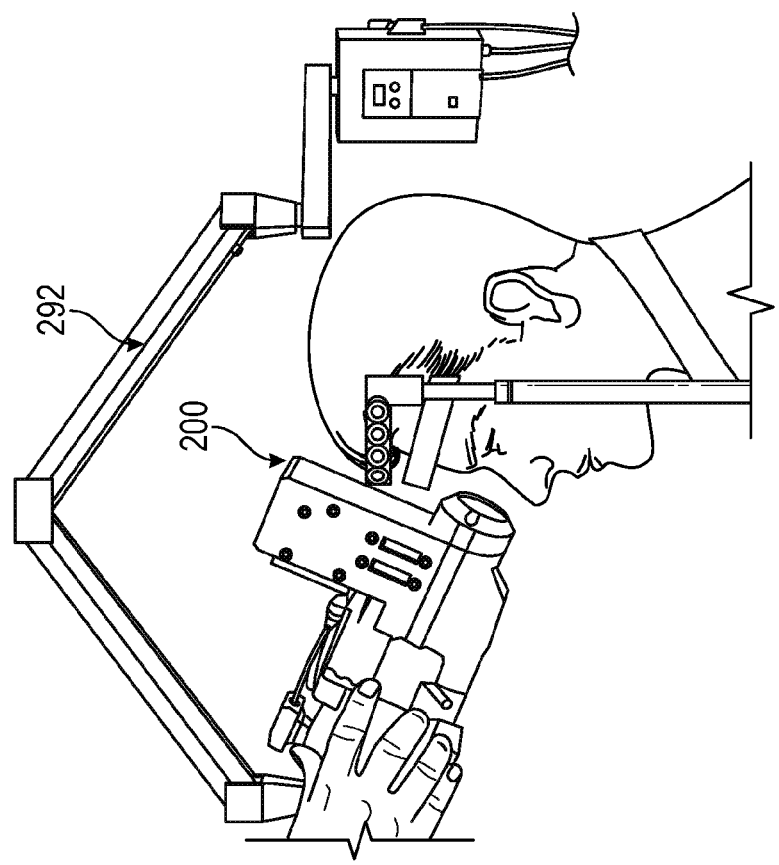
FIG. 4 depicts an alternate embodiment of the present invention comprising a retinal camera with embedded computing unit module, chin rest, and wall-mounted articulated camera mount.
Figure 3:
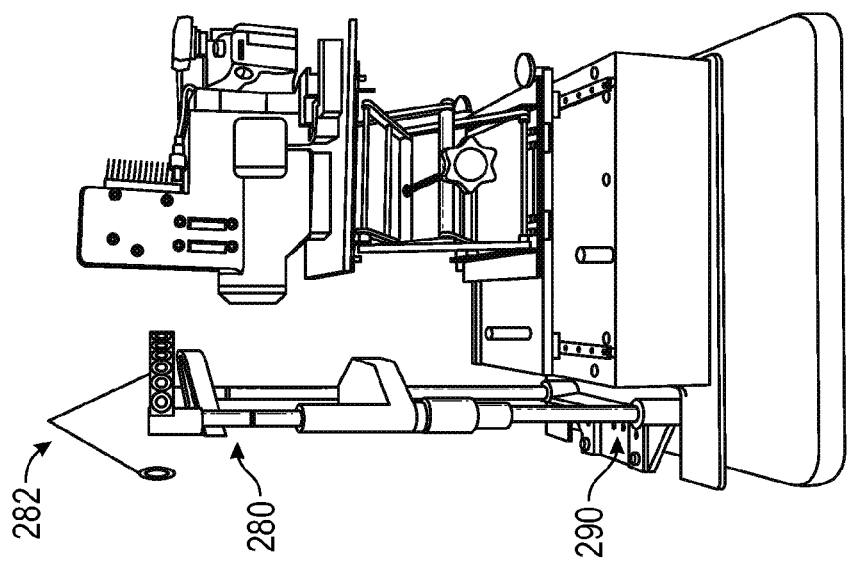
FIG. 3 depicts a first embodiment of the present invention comprising a retinal camera with embedded computing unit module, chin rest, camera base, and external fixation light.
Figure 5:
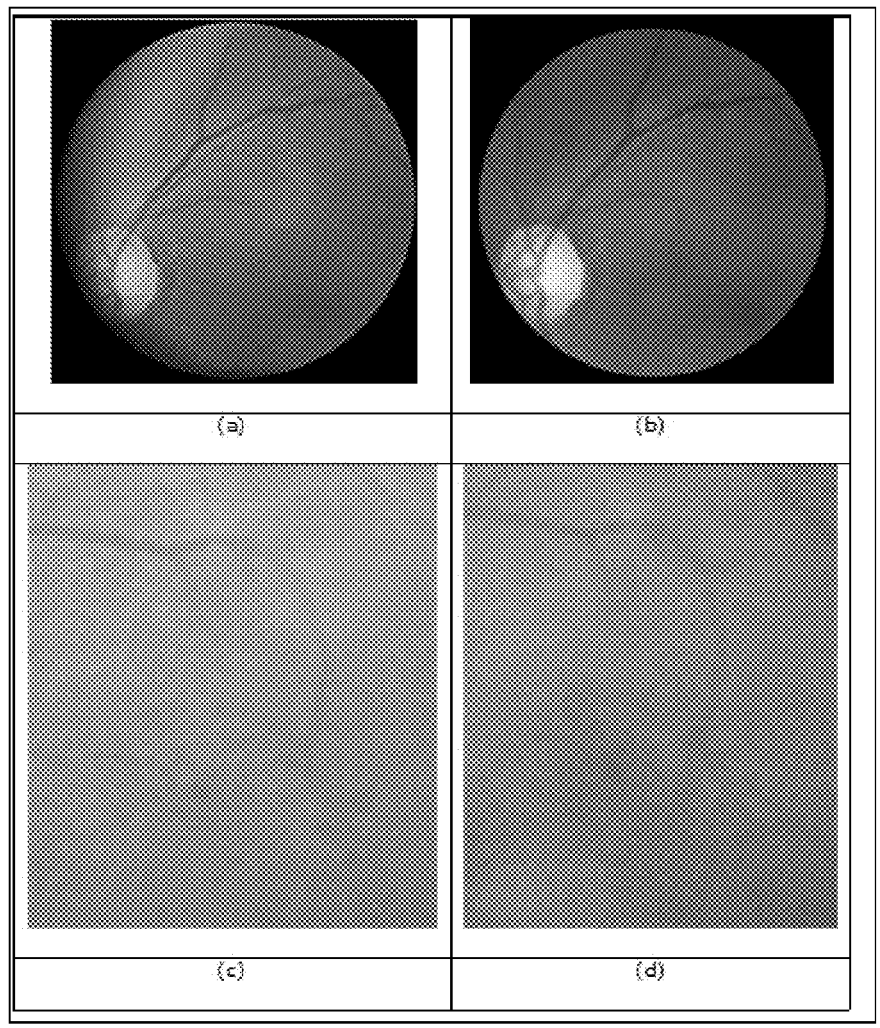
FIG. 5 depicts a set of sample images of adequate quality of a subject with advanced diabetic retinopathy.
Figure 6:
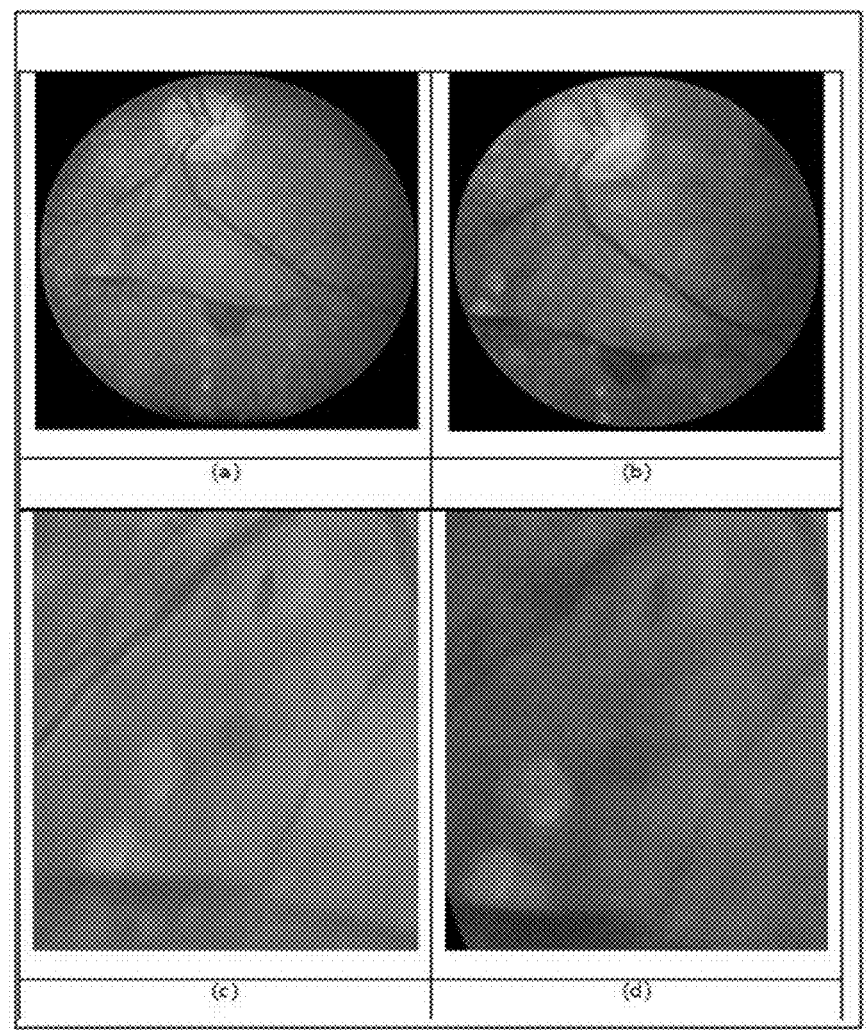
FIG. 6 depicts a set of sample images of adequate quality of another subject with advanced diabetic retinopathy.

FIG. 3 illustrates an example of retinal camera 200 setup that can be used to provide spatial stabilization between the imaging target 100 and the retinal camera 200. This example comprises chin rest 280 and camera mount 290. In one embodiment of the retinal camera an external fixation light 282 can be attached to the chin rest to allow precise control of the subject's gaze in order to image different areas of the fundus. FIG. 4. illustrates an example of retinal camera 200 that comprises a wall-mounted camera base 292 to enable relative stabilization between the imaging target 100 and the retinal camera 200. FIGS. 5-6 are example images of adequate quality acquired with two different retinal cameras from two diabetic individuals presenting advanced stages of diabetic retinopathy.

Referring to FIG. 2, Image Quality Analyzer 300 preferably performs real time and automatic assessment of retinal images transmitted by the transmission system 270. The Image Preparation process 310 preferably comprises one or more image processing phases such decoding of video into images, image resizing, image enhancement, and color channel transformation. The Image Preparation process 310 preferably uses one or more methods implemented as machine-coded algorithms and running on a computing unit 600 comprising one or more types of host memory 610, one or more types of host processors 620, and one or more types of graphics processing units 630. Examples of the methods used in the Image Preparation process 310 include those found in scientific calculation software tools such as Matlab and its associated toolboxes.

Figure 12:
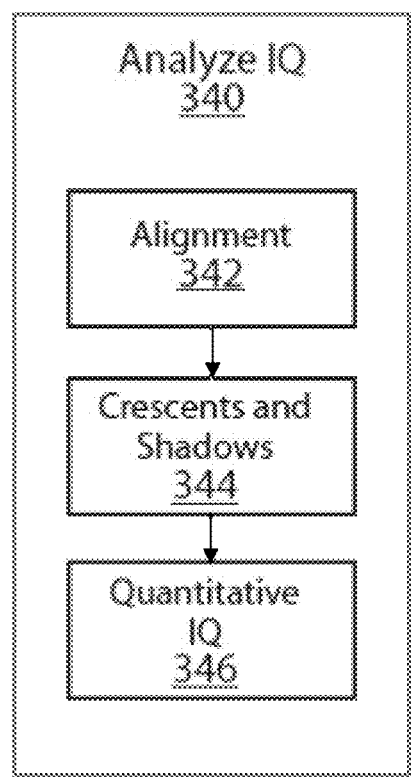
FIG. 12 depicts the steps of the Analyze Image Quality module 340.

The Analyze Image Quality phase 340, detailed in FIG. 12, uses one or more tools or applications to determine one or more image quality characteristics in retinal images. Said tools or applications are preferably implemented as machine-coded algorithms running in a computing unit 600. In an embodiment of the Retinal Screening process, the Analyze Image Quality phase 340 determines retinal image alignment through the Alignment phase 342, the presence and extent of crescents and shadows through the Crescent and Shadow phase 344, and a measure of quantitative image quality according to expert visual perception through the Quantitative Image Quality phase 346. The results of the Alignment 342, Crescent and Shadow 344, and Quantitative Image Quality 346 phases are preferably passed to the Classification phase 350 for further processing.

Figure 10:
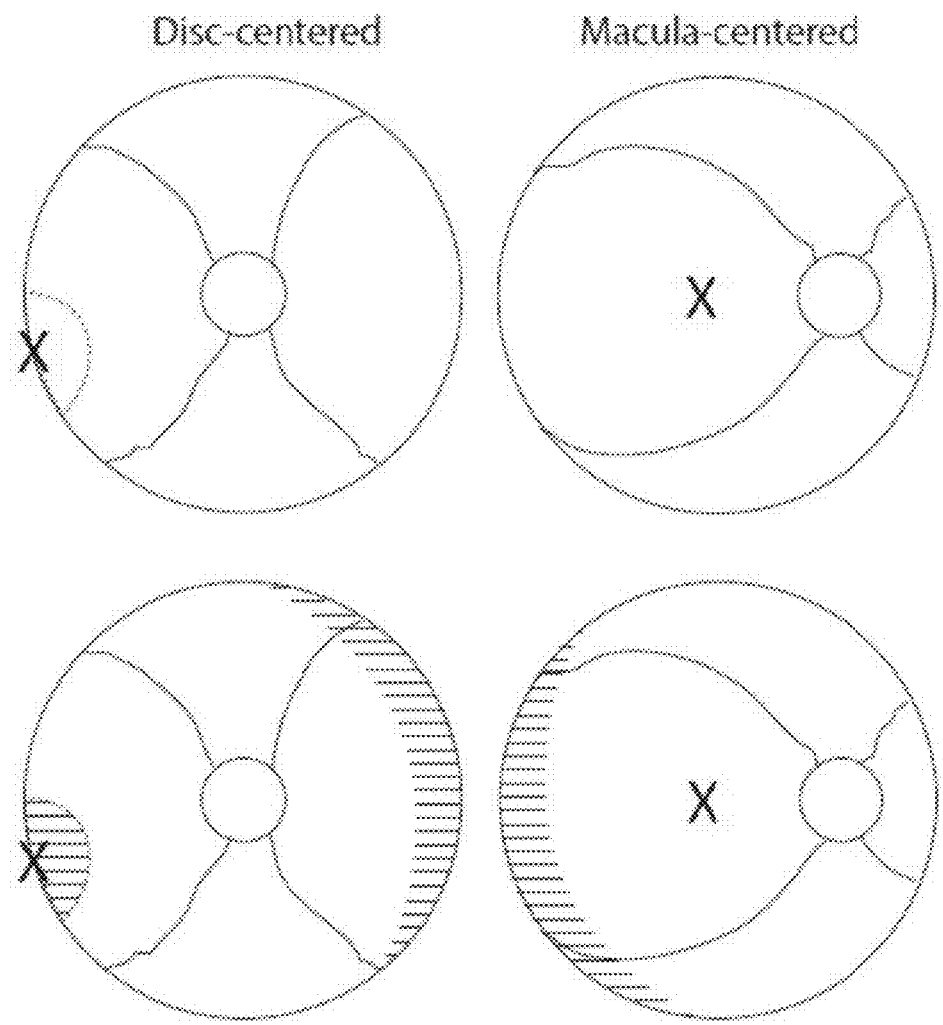
FIG. 10 depicts retinal images with adequate image quality.
Figure 11:
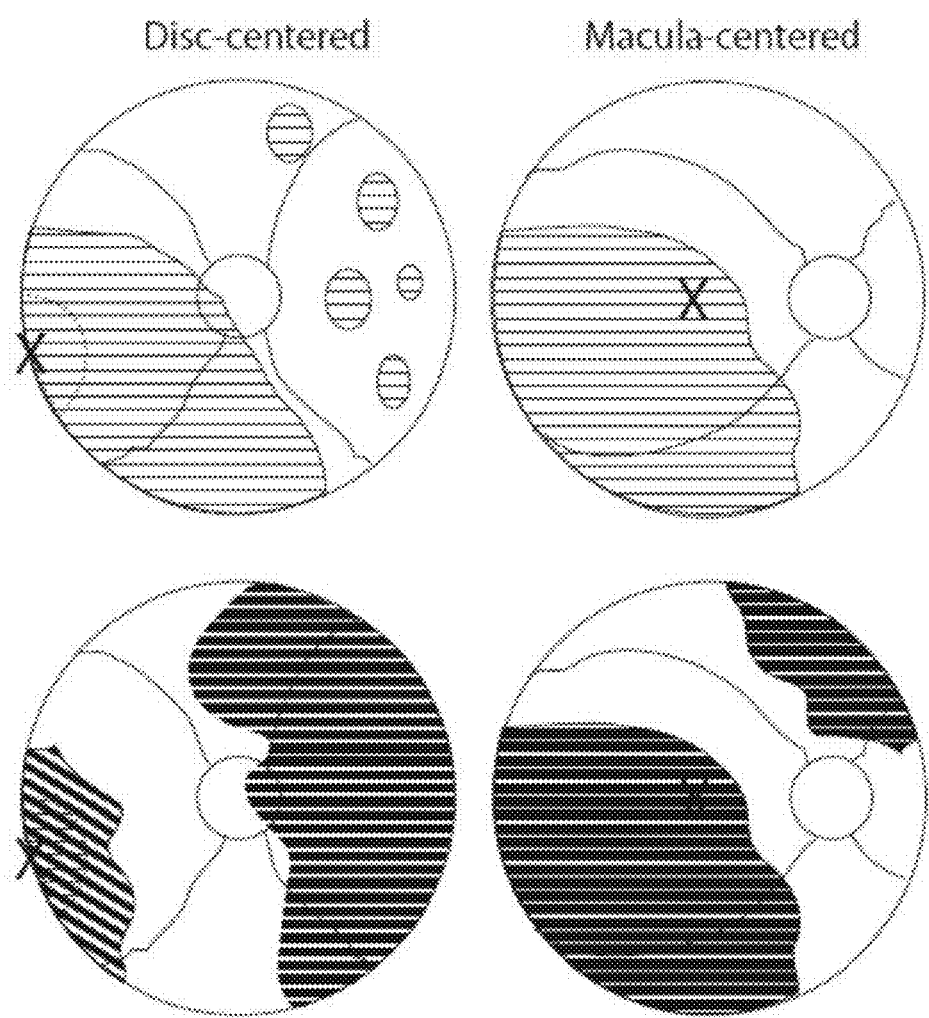
FIG. 11 depicts retinal images with inadequate image quality.

The Alignment phase 342 preferably automatically determines whether a retinal image complies with an imaging protocol. If a retinal image does not comply with said imaging protocol the Alignment phase 342 determines that said image is misaligned. An embodiment of the imaging protocol uses one retinal image with the optic disc in the center of the image (herein referred to as F1) and image with the fovea in the center of the image (herein referred to as F2). FIGS. 10 and 11 depict examples of F1 and F2 images. Examples of rules for image quality criteria using both F1 and F2 images are listed in Table 1. The Alignment phase 342 preferably uses one or more image processing steps implemented as machine-code algorithms running in computing unit 600, and preferably comprises the steps of field detection, macula detection 710, right/left eye detection 720, and alignment check 730.

The Field Detection phase preferably uses one of more machine-coded algorithms running in a computing unit 600 to determine whether a retinal image is F1 or F2. The Field Detection phase determines the location of the optic disc and relates this location to areas on the retinal image where the optic disc should be located for F1 images and F2 images. A region of interest with respect to the field of view (FOV) center (white square) is defined as shown in FIG. 7. The region consists of a vertical band with width equal to two optic disc (OD) diameters. If the automatically detected optic disc location falls inside of this band, then the image is classified as F1. If the OD falls outside this band, it may not be a F1 image since it is farther away from the FOV center, relative to macula. If the OD is outside of the band on either side, there is a higher probability of macula being inside the band on the other side (given that the macula is approximately 2 optic disc diameters away from the OD, and the width of the band is 2 OD). Thus the macula is closer to the FOV center relative to the OD, and therefore it is a F2 image.

Figure 13:
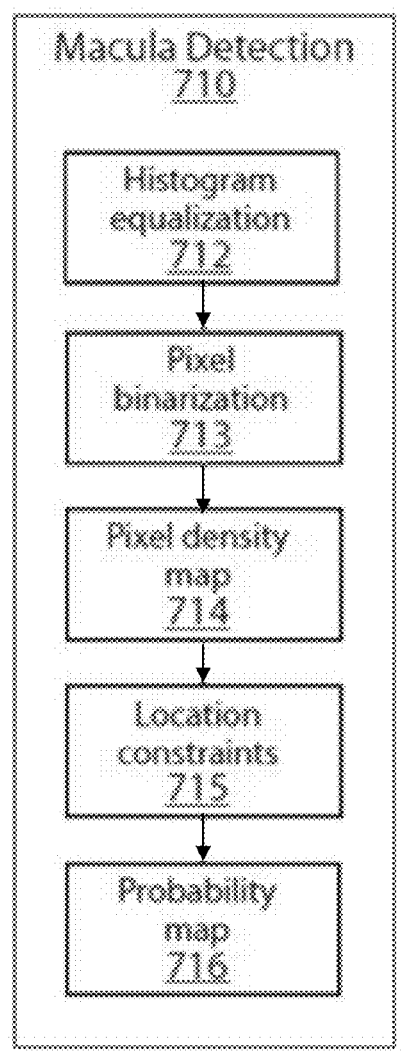
FIG. 13 depicts the steps for detecting the macula 710 in a fundus image.

Macula Detection step 710 uses one or more machine-coded algorithms running in a computing unit 600 to determine the location of the macula within a retinal image. As shown in FIG. 13, an embodiment of Macula Detection step 710 preferably comprises histogram equalization step 712 to enhance image contrast, pixel binarization step 713 to eliminate gray scales, pixel density map step 714 to determine the region with the highest pixel density within the image, location constraints step 715 based on angular position with respect to optic disc location, and probability map step 716 to determine the most likely candidate pixels represent the macula. The most likely pixel on step 716 is then preferably assigned the machine-calculated macula location. FIG. 8 illustrates an example of the probability map resulting from the steps carried out by the Macula Detection step 710 on a retinal image.

Figure 9A:
FIG. 9A illustrates a retinal image and FIG. 9B shows the portion of the optic disc analyzed by the Left/Right Detection step 720, which uses vessel density on the optic disc to determine the side of the retinal image shown in FIG. 9A. The optic disc has a lower vessel density on the right, so the temporal edge of the optic disc is on the right of the retinal image, and the retinal image is labeled as a "left" image.
Figure 9B:
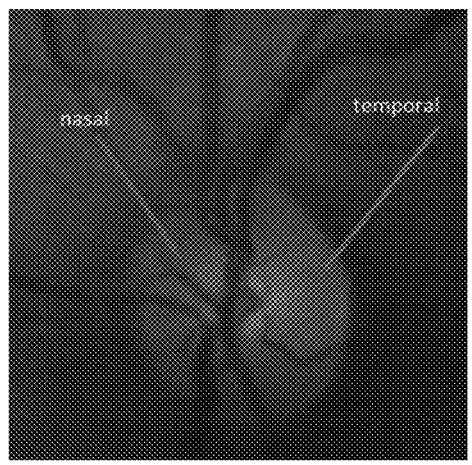
Figure 14:
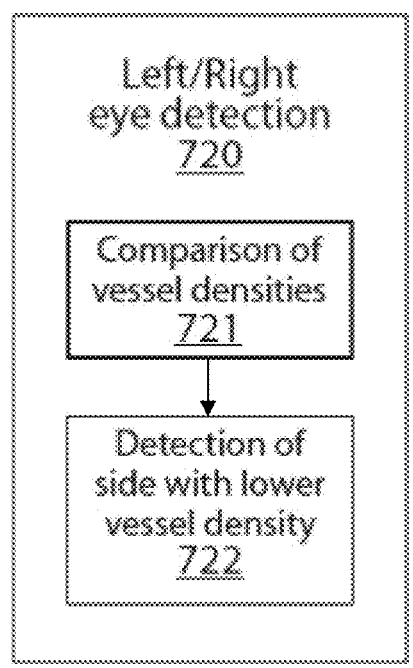
FIG. 14 depicts the steps for detecting if a retinal image belongs to a right or left eye 720.

Left/Right Eye Detection step 720 preferably uses one or more machine-coded algorithms running in a computing unit 600 to determine the side of the face a retinal image belong to. As shown in FIG. 14, Left/Right Eye Detection step 720 preferably analyzes the vessels within the optic disc, and step 721 compares the vessel density in the left half of the optic disc to the vessel density in the right half of the optic disc. The half with the lower vessel density is labeled as the temporal edge of the optic disc in step 722. If the temporal edge of the optic disc is on the right side of the retinal image then the retinal image is labeled as "left". If the temporal edge of the optic disc is on the left side of the retinal image then the retinal image is labeled as "right". FIG. 9 illustrates an example of a "left" retinal image and the nasal and temporal edges of the optic disc.

Figure 15:
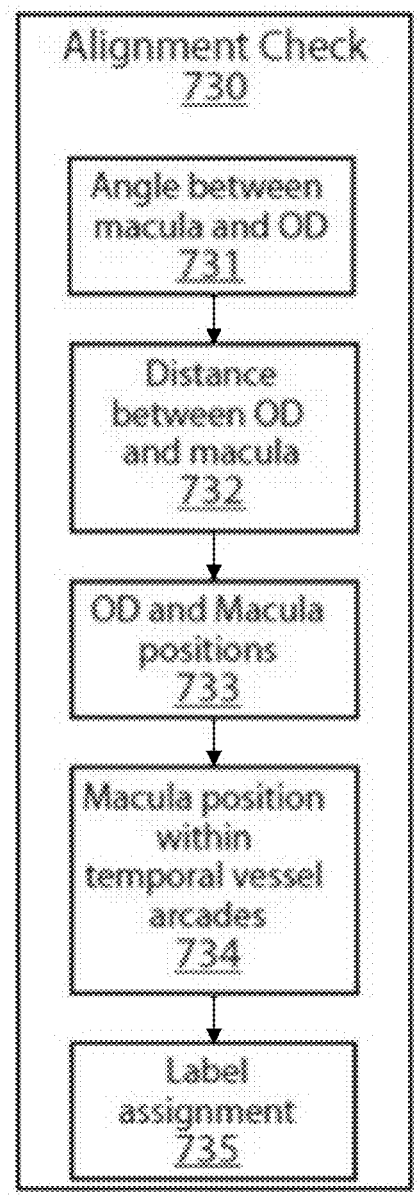
FIG. 15 depicts the steps to check whether a retinal image is correctly aligned 730 according to a pre-determined protocol.

Alignment Check step 730 preferably uses one or more machine-coded algorithms running in a computing unit 600 to determine whether a retinal image is correctly aligned. An embodiment of Alignment Check step 730 is illustrated in FIG. 15 and comprises step 731 to check that the macula position is at an angle between 0 degree and 20 degrees below the position of the optic disc with respect to the horizontal axis of the retinal image, step 732 to check that the distance between the optic disc center and the macula is more than two optic disc diameters and less than three optic disc diameters, step 733 to check that the optic disc and macula are positioned within one-third and two-thirds sections of the vertical image size, and step 734 to check that the macula is positioned within the vertical region limited by the temporal vessel arcades. When a retinal image passes the aforesaid checks, it is assigned two labels in step 735, one for eye side and one for field of view. The eye side label is preferably "OD" if it is a right eye image or "OS" if it is a left eye image. The field of view label is preferably "F1" if it is a disc-centered image or "F2" if it is macula-centered image. An image that fails one or more checks is preferably assigned the label "Misaligned" or "unacceptable".

Figure 16:
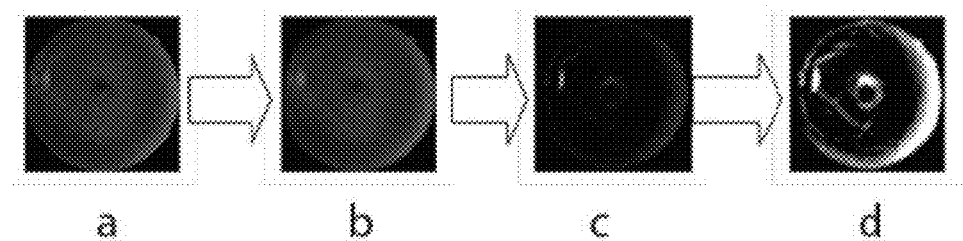
FIG. 16 depicts gradient and filtering processing steps for detecting crescents in a retinal image.
Figure 17:
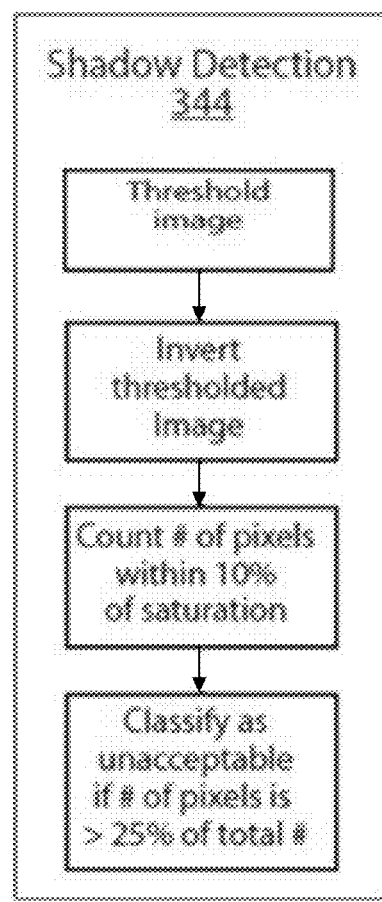
FIG. 17 depicts the steps to detect shadows 344 in a retinal image.

Crescent/Shadow Detection step 344 is illustrated in FIG. 17 and preferably uses one or more machine-coded algorithms running in a computing unit 600 to determine whether a retinal image includes crescents and/or shadows. Crescents occur from iris reflection due to small pupils or misalignments by the photographer. The reflected light shows up as a bright region towards the edge of the image. The brightness of the crescent is generally strongest at the boundary of the image and fades toward the center of the image. Shadows are caused by not enough light reaching the retina and creating dark regions on the images. Both crescents and shadows obscure parts of the retina that may have important clinical information. For crescent detection, embodiments of Crescent/Shadow Detection step 344 comprise creating a mask that contains the retinal image, applying a gradient filtering algorithm to detect gradual changes in pixel value towards the center of the image, enhancing the gradient image, and determining whether the number of pixels in the third quartile of the gradient image occupy more than a preferable percent (e.g. 15%) of the image area as illustrated in FIG. 16. When the number of pixels in the third quartile of the gradient image occupies more than the predetermined percent of the image area the image is assigned the label of "inadequate". It will be known to those skilled in the art that different combination of masks, gradient image, percentiles, and areas covered by crescents may be used in the present invention. For shadow detection embodiments of Crescent/Shadow Detection step 344 comprise applying a pixel value threshold to the pixels of the retinal image, inverting the values of the thresholded image, counting the numbers of pixels within 10 percent of saturation, and comparing this number of pixels to 25 percent of the total number of pixels in the retinal image. When the number of pixels within 10 percent of saturation in the thresholded image is preferably larger than 25 percent of the total number of pixels in the image, the image is assigned the preferably label "inadequate." It will be known to those skilled in the art that different combinations of threshold values, percentiles, and areas covered by shadows may be used in the present invention.

Figure 18:
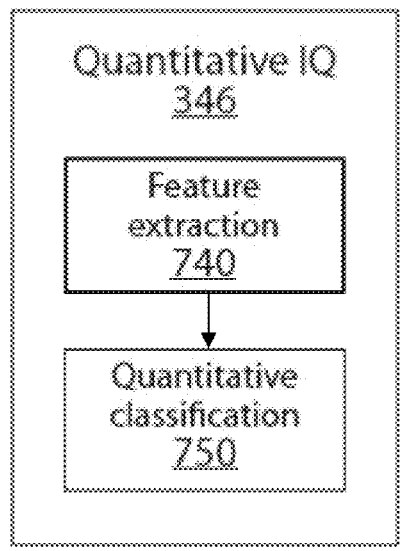
FIG. 18 depicts the steps for quantitative image quality determination 346.

Embodiments of the present invention preferably provide an automated approach based on the classification of global and local features that correlate with the human perception of retinal image quality as assessed by eye care specialists. Quantitative Image Quality step 346 preferably uses one or more machine-coded algorithms running in a computing unit 600 to determine whether a retinal image includes image quality defects associated with visual perception of human experts. FIG. 18 depicts the embodiment steps of quantitative image quality determination feature extraction 740 and quantitative classification 750. Visual perception information comprises a dataset set of retinal images which have been assigned labels by expert readers of retinal images. Said labels are preferably "adequate" for retinal images that include adequate quality and "inadequate" for retinal images that do not include adequate quality. Adequacy comprises the expert's subjective assessment of whether an image includes adequate quality to make a clinical determination including but not limited to presence of lesions that may indicate the presence of disease. The dataset of images and associated labels is used as a training set for quantitative classification 750.

Figure 19:
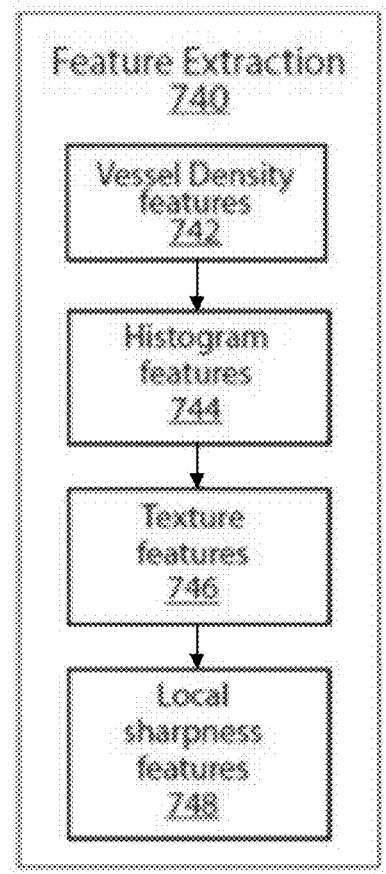
FIG. 19 depicts the steps for image quality feature extraction 740 in a fundus image.

Feature extraction 740 comprises calculation of mathematical image features of one or more categories. As shown in FIG. 19, an embodiment of feature extraction 740 comprises four categories: vessel density features 742, histogram features 744, texture features 746, and local sharpness features 748. The overall image content, such as lightness homogeneity, brightness, and contrast are preferably measured by global histogram and textural features. The sharpness of local structure, such as optic disc and vasculature network, is preferably measured by a local perceptual sharpness metric and vessel density. It will be known to those skilled in the art that different categories of mathematical image features and combinations thereof are possible and are all part of the present invention.

Vessel density features 742 are used in order to check the sharpness of dark vessel structures since the performance of vessel segmentation is sensitive to the blurriness of vasculature. To segment the retinal vascular, a method based on Hessian eigen system and the second order local entropy thresholding can be used (H Yu, S Barriga, C Agurto, G Zamora, W Bauman and P Soliz, Fast Vessel Segmentation in Retinal Images Using Multiscale Enhancement and Second-order Local Entropy, accepted by SPIE medical imaging, February, 2012, San Diego, USA), Vessel segmentation is performed after illumination correction and adaptive histogram equalization to remove uneven lightness and enhance contrast in the green channel of the retinal images. FIG. 20 shows an example of vascular segmentation. Vessel density is preferably calculated as the ratio of the area of segmented vessels over the area of field of view (FOV) in an image.

Preferably seven histogram features 744 are extracted from the two or more color spaces, e.g. RGB: mean, variance, skewness, kurtosis, and the first three cumulative density function (CDF) quartiles. These seven histogram features describe the overall image information such as brightness, contrast, and lightness homogeneity. Computed first order entropy and spatial frequency may also be used to detect the image complexity.

Texture features 746 are used in identifying objects in an image. The texture information can be obtained by computing the co-occurrence matrix of an image. Preferably five Haralick texture features are calculated: the second order entropy, contrast, correlation, energy and homogeneity (Haralick, R. M., K. Shanmugan, and I. Dinstein, "Textural Features for Image Classification", IEEE Transactions on Systems, Man, and Cybernetics, Vol. SMC-3, 1973, pp. 610-621). Entropy measures the randomness of the elements of the matrix, when all elements of the matrix are maximally random, entropy has its highest value. Contrast measures the intensity difference between a pixel and its neighbor. The correlation feature measures the correlation between the elements of the matrix. When correlation is high the image will be more complex than when correlation is low. The fourth feature, energy describes the uniformity of the texture. In a homogeneous image there are very few dominant grey-tone transitions, hence the co-occurrence matrix of this image will have fewer entries of large magnitude. So the energy of an image is high when the image is homogeneous. The last feature, homogeneity, also called inverse difference moment, has a relatively high value when the high values of the co-occurrence matrix are near the main diagonal. It is a measure of coarseness in an image.

A clear and sharp edge is important for good quality of an image. A local sharpness metric 748, the cumulative probability of blur detection (CPBD), is applied on the green channel to measure the strength of sharp edges in the images. Average edge width and gradient magnitude have been used to measure blurriness of images, but these have been found to be too simplistic to directly correspond to human visual perception of blurriness, which is a complicated process. An embodiment of the local sharpness feature step 748 uses the cumulative probability of blur detection (CPBD) at every edge (N. D. Narvekar and L. J. Karam, "A No-Reference Image Blur Metric Based on the Cumulative Probability of Blur Detection (CPBD)," IEEE Transactions on Image Processing, Vol. 20 (9), 2678-2683, September 2011). CPBD assumes that the blurriness around an edge is more or less noticeable depending on the local contrast around that edge. It derives a human perceptibility threshold called "Just Noticeable Blur" (JNB), which can be defined as the minimum amount of perceived blurriness around an edge given a contrast higher than the "Just Noticeable Difference" (JND). The perceived blurriness around an edge is counted only when its amount is larger than the "Just Noticeable Blur" under Just Noticeable Difference" in contrast. It can be modeled as follows:

$$P_B(e_i) = 1 - e^{-\left|\frac{w(e_i)}{w_{JNB}(e_i)}\right|^{\beta}}$$

where $P_B(e_i)$ is the probability of blur detection at each edge $e_i$. If the actual width of the edge is the same as the JNB edge width, then $P_B(e_i)=63\%$, below which blur is said to be undetectable. β has a median value of 3.6 based on an experimentally determined psychometric function (Ferzli, R. Karam, L. No-reference Objective Image Sharpness Metric Based on the Notion of Just Noticeable Blur IEEE Transactions on Image Processing. pp. 717 728. 2009). The cumulative probability is based on the sum of the blur probabilities that are below 63%. The CPBD value is therefore negatively correlated to the edge blurriness. To measure the local edge blurriness, the image is divided into blocks of a size of 64×64. And the ratio of edge blocks, in which the number of edge pixels is more than a certain threshold, over the number of all blocks, is used as another feature since some hazy retinal images due to cataract may appear foggy and misty with sharp edge underneath. The top row of FIG. 21 shows three example images; the bottom row contains their corresponding intensity profiles across a vessel segment. The cataract image shown in FIG. 21C has a higher CPBD value than the good quality image shown in FIG. 21A because of the edge sharpness.

Quantitative Classification 750 preferably comprises a dataset of reference labels of image quality and associated mathematical features to produce a mathematical predictor of image quality. Further, Quantitative Classification 750 preferably comprises a mathematical predictor of image quality to predict the image quality label of an image using said image's mathematical features. In an embodiment of the present invention a predictor of image quality is constructed by determining the relationship between the reference set of image quality labels and their associated mathematical features. To predict the image quality label of a retinal image, the predictor of image quality uses said relationship to assign said image a label of either "adequate" or "inadequate" on the basis of the mathematical features of said image. An embodiment of the mathematical predictor of image quality comprises a partial least squares (PLS) classifier. PLS is a very powerful method of eliciting the relationship between one or more dependent variables and a set of independent (predictor) variables, especially when there is a high correlation between the input variables. In the present invention, the same feature when applied to different color channels tends to be highly correlated even if their magnitudes are quite different. PLS finds a lower dimensional orthogonal sub-space to the multi-dimensional feature space and provide robust prediction. It will be known to those skilled in the art that other prediction models exist and can be used alone or in combinations to obtain labels of image quality.

Experimental results from application of one of the embodiments of the present invention as described herein have shown its utility in determining image quality of retinal images and are explained in the next paragraphs A data set of digital fundus photographs from 412 subjects (1884 images) was captured with a Canon CR1 Mark II camera. The images are macula-centered or optic disc centered, 45 degree field of view, non-mydriatic images of both eyes with a dimension of 4752×3168 pixels. The image quality grading was provided by two optometrists. The graders assigned each image to one of four quality categories: high, medium, low, and reject based on overall illumination, image contrast, sharpness of fine structure, illumination on the macula, and grader's confidence on ability to identify lesions. The purpose of image quality evaluation is to detect the low quality images whose quality is inadequate for DR screening. Reject and low quality images were grouped into the inadequate category while medium and high quality images were grouped into the adequate category for providing the reference standard for the classification.

To show the effectiveness of the present invention, different feature sets were tested. The isolated features (histogram, texture features, and blurriness features), and a combination of all features were tested. All features were normalized to zero mean and unit standard deviation before classification.

In the experiment, 28% of 1884 images were labeled as inadequate quality. External shots of the pupils were not excluded from the data set and were labeled as inadequate quality. Statistical significance tests of the difference between ROC curves were performed. The sensitivity for classifying inadequate quality images at a specificity of 80% using leave-one-out validation is given in Table II.

The blurriness features (including vessel density and CPBD metrics) achieved the best performance of the selected subsets of features (92.6% of AUC). The highest classification performance is achieved by the final combination of all the features (95.8% of AUC). The tests of the difference between the areas under the ROC curves were performed by using Metz ROC Software (http://metz-roc.uchicago.edu/MetzROC). The difference between all features and the isolated features was found to be significant with a $p$ value less than 0.00005.

The performance of automated image quality evaluation is satisfactory considering the diversity of the images in the data set. This embodiment of the present invention was tested on 824 macula-centered images selected from the above data set. There are 97 images marked as inadequate quality, which is 12% of the 824 images. Results of this test are shown in Table III. The performance of the classifier using all features is significantly better than any isolated feature at the significant level of 95%. Because only macula-centered images were used in this experiment, the diversity of image contents was reduced; a higher AUC was achieved at 98.1%. But the standard deviation of AUC is slightly larger than that in the experiment where 1884 images were used.

To validate this embodiment of the present invention, a ten-folded cross-validation method was applied. Images were randomly chosen for each of the ten subsets. Each image was tested exactly once in the experiment. The average AUC for the ten runs for training and testing were 96.5% and 95.3%, respectively for 1184 images. For 824 macula-centered images, the average AUC of the ten runs for training and testing were 98.3% and 97.5%, respectively. The classification results are consistent when going through multiple rounds of cross-validation using difference data partitions. This indicates that the extracted features are effective in separating the images into two classes.

Fleiss' kappa correlation was calculated between the reference standard and the results generated by this embodiment of the present invention. We used the threshold that obtained the sensitivity of 95.3% at the specificity of 80%. The inter-observer correlation between the two different human observers was 0.25, while the correlation between the reference standard and the automated method was 0.72. The kappa value was also calculated by adding the automated method's results as a third observer's results to test the agreement. The initial inter-observer correlation (k=0.25) is increased to 0.43 for assuming the automated method to be an additional observer. The difference between the reference standard and the results of the proposed automated method is less than the inter-observer variability.

These results indicated that an image quality screening method according to an embodiment of the present invention performs well by using global image appearance features and local sharpness measures. Due to the large variability presented in the data set, the content of the images is very heterogeneous; thus reducing the effectiveness of histogram and Haralick features in quality evaluation. Vessel density and local CPBD features enhance the system performance by used as effective measures of image structure blurriness.

The Wilcoxon rank sum and Ansari-Bradley test were also used to determine whether the adequate and inadequate quality classes' median values and dispersions (e.g. variances) differed significantly. If neither the median nor the dispersion differ significantly between adequate and inadequate classes, the feature is unlikely to be useful for classification. The selected histogram features and Haralick features were used. However, a decreased performance was presented. So no feature reduction was applied in the final classification.

Since the image quality may appear differently in localized areas of a retinal image, an alternate experiment in which all the features were extracted from three regions of interest (ROI) was performed: optic disc region, upper retinal and lower retinal hemispheres. However, the final performance of the image quality screening experiment using ROIs was slightly worse as measured by AUC than the system using global features with a $p$ value of 0.4793. Using the bivariate binormal model, the shape of ROCs was not significantly different with a $p$ value of 0.1145.

In summary, the experimental results presented herein show an automated method to screen for image quality that integrates global histogram and texture features, as well as local sharpness features. By introducing local sharpness criteria, the performance of the system was increased even if the image contents exhibited large heterogeneities. Overall, the experimental results described herein show that embodiments of the present invention have the potential to provide an efficient, objective and robust tool in retinal image quality evaluation for broad screening applications.

TABLE II

Results of the classifier using different features for total 1884 images

|  | AUC (Std) | 95% CI | Sensitivity (Specificity of 80%) | p value |
|---|---|---|---|---|
| Histogram | 82.2% (1.06%) | (80.1%, 84.2%) | 70.2% | 0.0000 |
| Haralick | 72.3% (1.32%) | (70.0%, 75.1%) | 53.5% | 0.0000 |
| Blurriness | 92.6% (0.63%) | (91.4%, 93.9%) | 89.3% | 0.0000 |
| All features | 95.8% (0.44%) | (94.8%, 96.6%) | 95.3% | — |

TABLE III

Results of the classifier using different features for 824 macula-centered images

|  | AUC (Std) | 95% CI | Sensitivity (Specificity of 80%) | p value |
|---|---|---|---|---|
| Histogram | 92.9% (1.43%) | (89.8%, 95.5%) | 91.7% | 0.0001 |
| Haralick | 81.6% (2.27%) | (77.0%, 85.9%) | 65.3% | 0.0000 |
| Blurriness | 96.4% (0.77%) | (94.7%, 97.8%) | 95.8% | 0.0017 |
| All features | 98.1% (0.46%) | (97.1%, 98.9%) | 99.0% | — |

Figure 22:
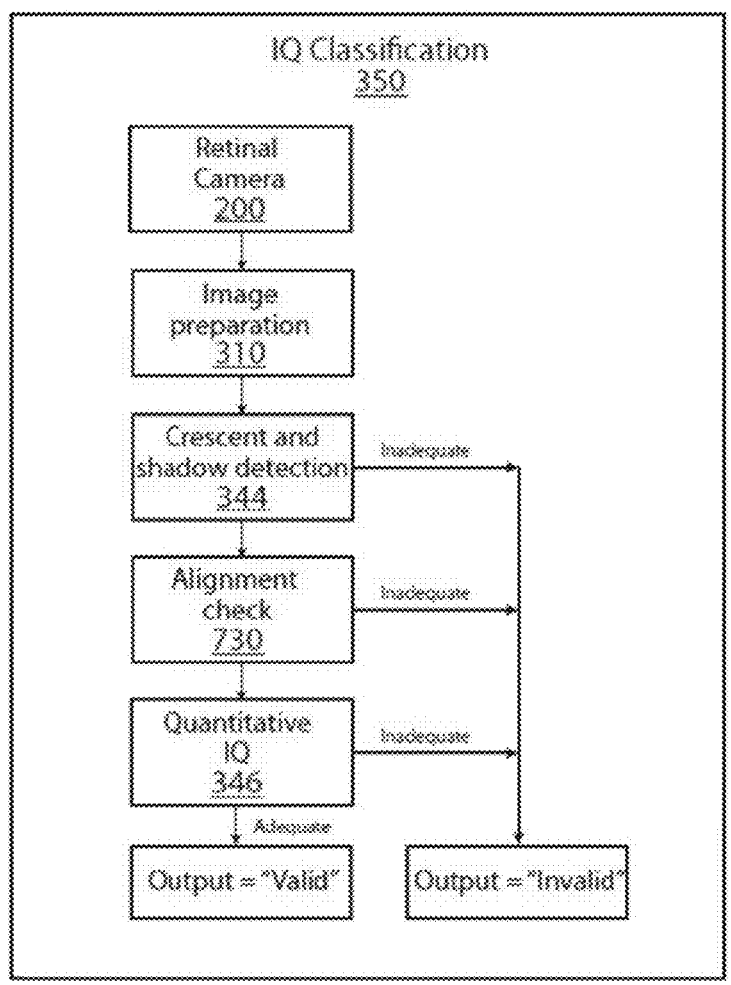
FIG. 22 depicts the steps for image quality classification 350 of a fundus image.

IQ Classification phase 350 is preferably implemented as machine-coded algorithms running in a computing unit 600, and preferably assigns a label to a retinal image that is indicative of its image quality and suggestive of an action that the photographer can take, such as "Valid" or "Invalid", "acceptable" or "unacceptable", "adequate" or "inadequate", or any other label obvious to anyone skilled in the art, to an RGB retinal image on the basis of the results from the Analyze Image Quality phase 340. As shown in FIG. 22, a label "Valid" is preferably assigned when the Crescent/Shadow step 344 outputs an "adequate" label, the alignment check step 730 outputs an "acceptable" label, and the Quantitative Classification 346 outputs an "adequate" label. A label "Invalid" is preferably assigned when any of the labels assigned by the Crescent/Shadow step 344, the alignment check step 730 outputs an "unacceptable" label, or the Quantitative Classification step 346 are "inadequate". When a retinal image is assigned a label "Invalid" the user should retake the image using the retinal camera 200.

Figure 23:
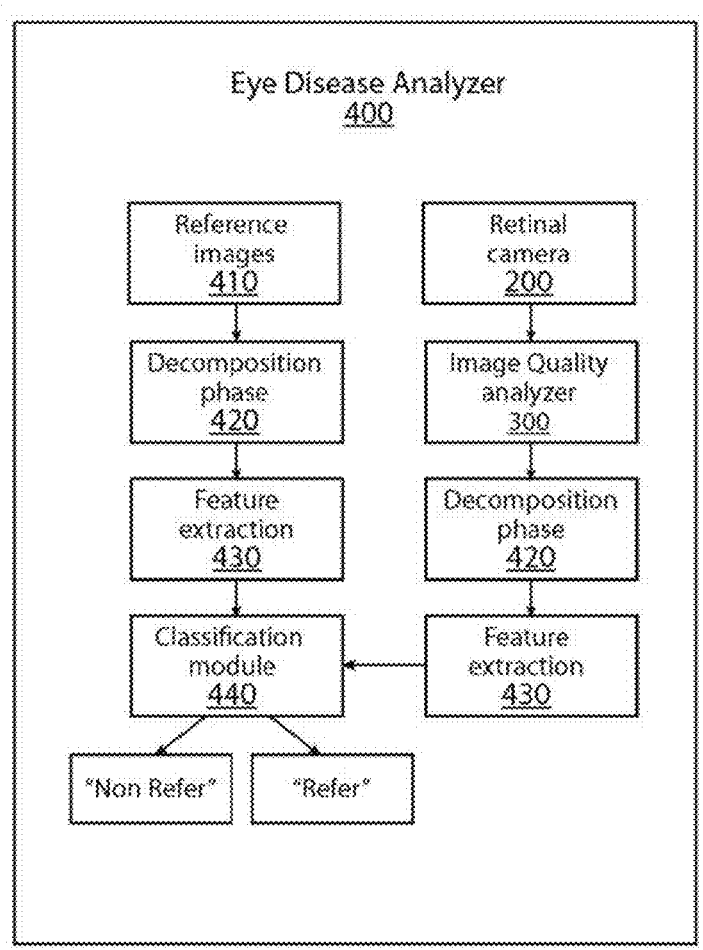
FIG. 23 depicts the steps for eye disease analysis 400 in a fundus image.

The Eye Disease analyzer phase 400 preferably processes one or more valid retinal images to determine whether said images include signs of disease. The Eye Disease analyzer phase 400 preferably comprises one or more machine-coded mathematical algorithms running in a computing unit 600 to assign a label to a retinal image indicative of the presence or absence of risk of disease. In an embodiment of the present invention, said labels are descriptive of the action to be taken by a health care provider on the basis of the presence of risk of disease, for example comprising "Refer" or "Non Refer". As shown in FIG. 23, an embodiment of Eye Disease analyzer phase 400 preferably comprises a set of Reference Images 410, a Decomposition phase 420, a Feature Extraction phase 430, and a Classification Model 440.

Figure 24:
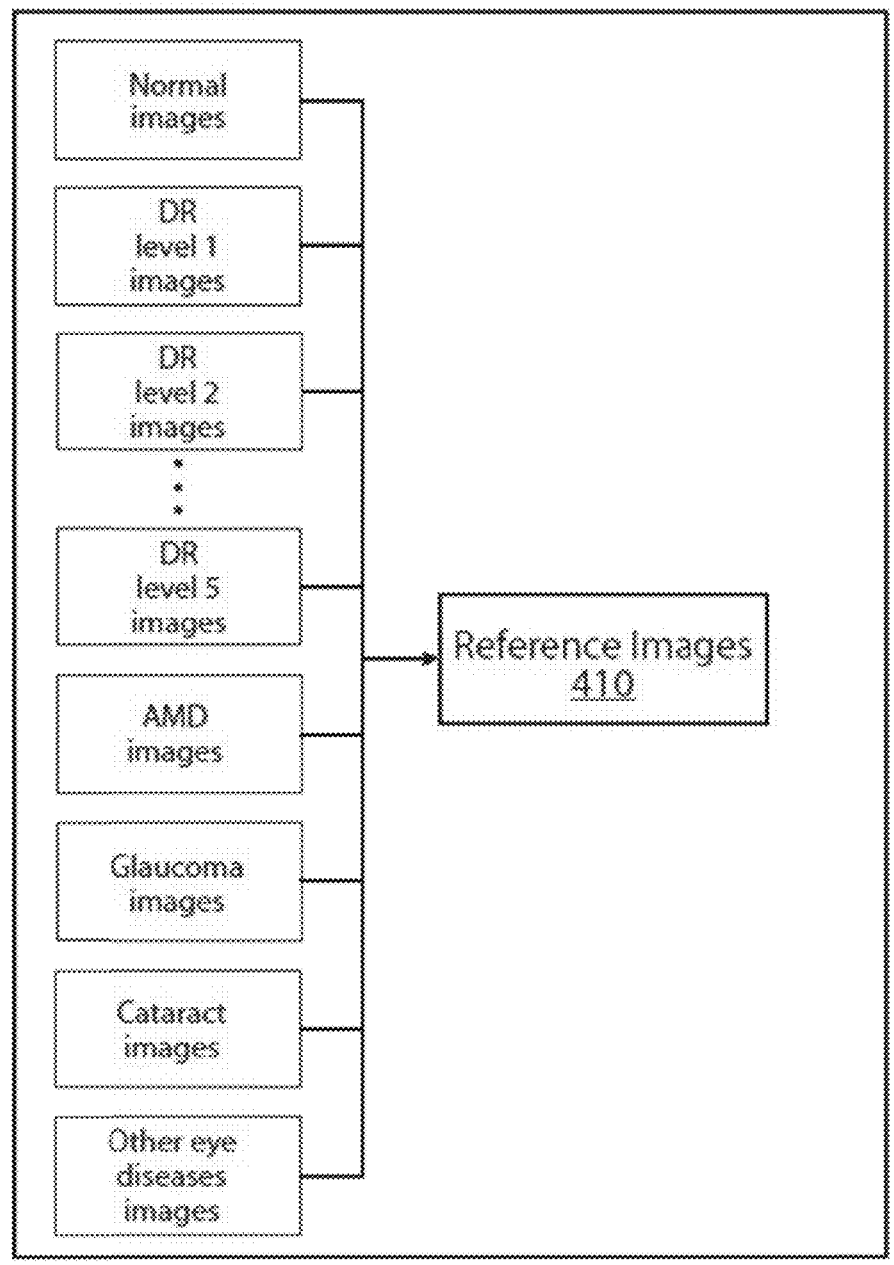
FIG. 24 depicts the elements that are part of the reference images 410.

The set of Reference Images 410 preferably comprises images containing a plurality of plausible grades of detectable disease comprising also cases of no detectable disease. As shown in FIG. 24, examples of diseases that these images can have include but are not limited to diabetic retinopathy (DR) levels 1 to 5, age-related macular degeneration (AMD), glaucoma, and cataracts. These images are used as examples of different types of detectable disease and as the basis for a Classification Module 440. The set of Reference Images 410 preferably further comprises descriptive labels according to the grades or detectable disease and these may be referred to as ground truth.

Figure 25:
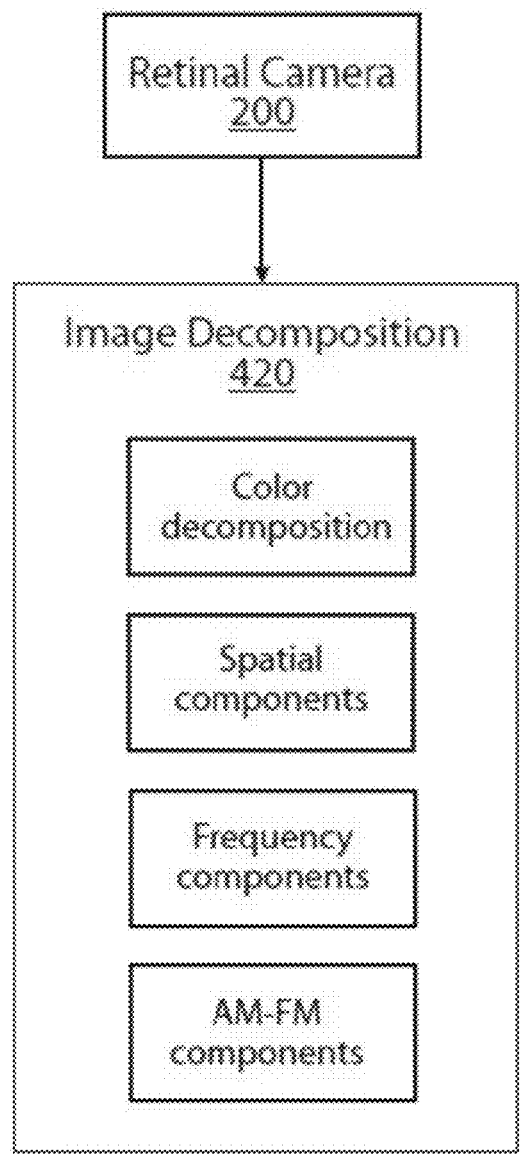
FIG. 25 depicts the elements that form the image decomposition step 420.

As shown in FIG. 25, Decomposition phase 420 preferably comprises one or more methods to decompose images into a plurality of color, spatial, and frequency components. In one embodiment of the present invention the Decomposition phase 420 comprises a multi-scale AM-FM filter bank that decomposes an image into its corresponding amplitude, frequency, and angle components for each pixel at a plurality of spatial scales, as described in U.S. Pat. No. 8,515,201.

Figure 26:
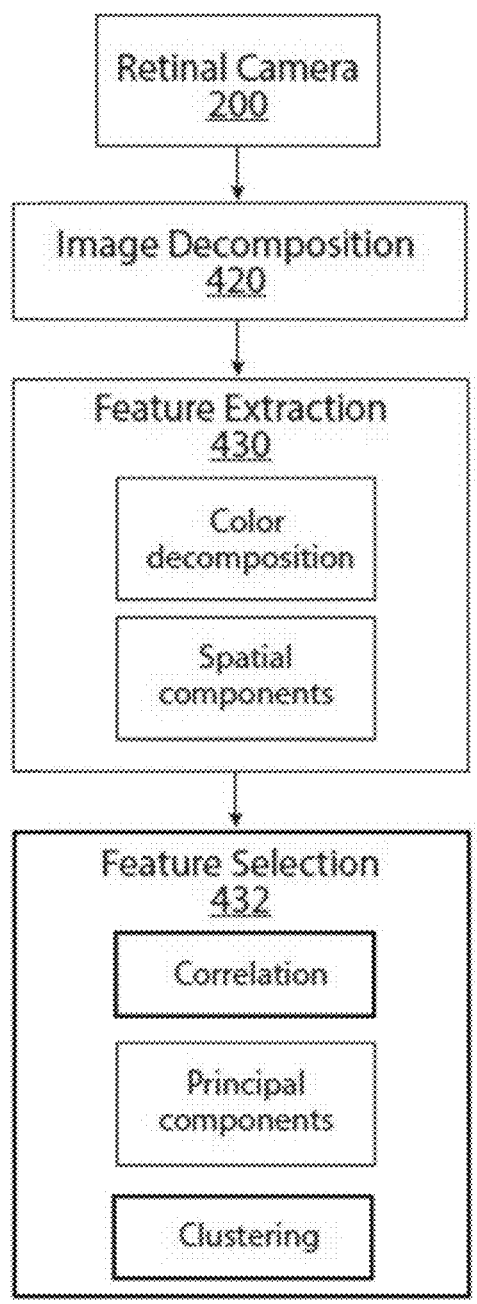
FIG. 26 depicts the elements of the feature extraction phase 430.

As shown in FIG. 26, Feature Extraction phase 430 preferably comprises one or more methods to group one or more decomposition components into concatenated series of components that can be referred to as feature vectors according to one or more grouping and discrimination methods. In one embodiment of the present invention, Feature Extraction phase 430 comprises grouping decomposition components into histograms and clusters according to their frequencies and measure of similarity, respectively. Feature Extraction phase 430 preferably comprises Feature Selection phase 432, which preferably comprises one or more methods to reduce the number of features according to selection criteria including but not limited to correlation, principal component analysis, or least squares, as described in U.S. Pat. No. 8,515,201.

Figure 27:
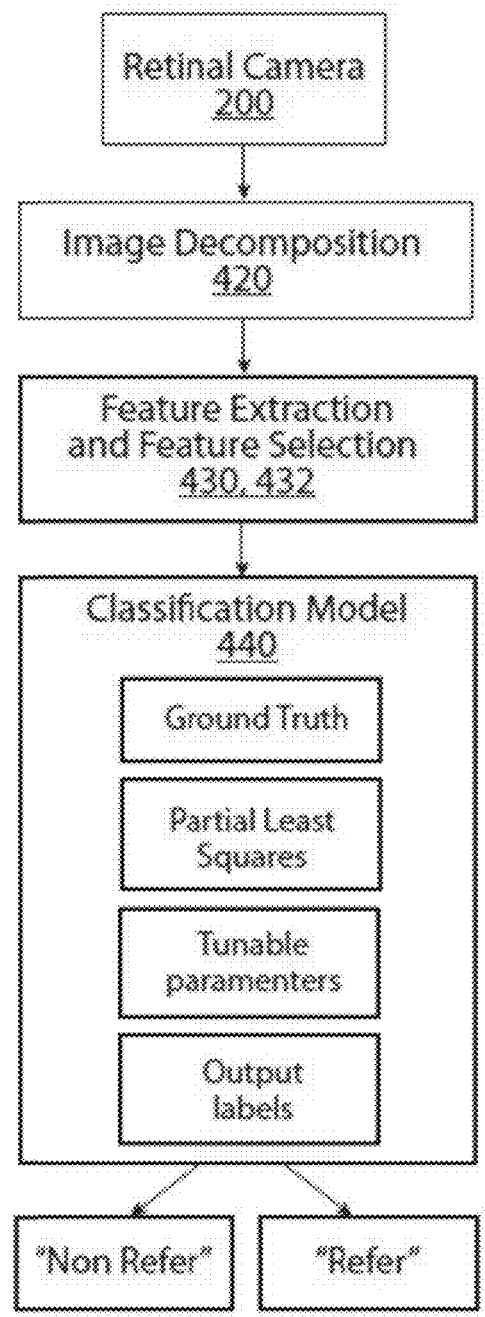
FIG. 27 depicts the steps for classification 440 of fundus images into "non-refer" (no eye disease) and "refer" (presence of eye disease).

As shown in FIG. 27, Classification Model 440 preferably comprises one or more methods to assign descriptive labels to images according to their features according to the Feature Extraction phase 430. When the Reference Images set 410 is used to create the Classification Model 440, one or more methods are used to associate the ground truth to the features in order to build the Classification Model 440. An embodiment of the classification model 440 using partial least squares to classify the images is described in U.S. Pat. No. 8,515,201. In one embodiment of the present invention Partial Least Square is used to associate the features from the Reference Images 410 to their corresponding ground truth.

When the Classification Model 440 is used on a "valid" image from the Classification phase 350, it preferably assigns a classification label that is descriptive of the presence of detectable disease on the image. In one embodiment of the present invention the Classification Model 440 assigns a label of "non Refer" to images that contain no detectable disease that represents a high risk of progressing to a threatening degree of disease within a certain amount of time, one year, for example. In this embodiment, the Classification Model 440 assigns a label of "Refer" to images that do contain detectable disease that represents a high risk of progressing to a threatening degree of disease within a certain amount of time.

In one embodiment of the present invention the Classification Model 440 comprises one or more tunable parameters to determine the assigning of labels to images. By tuning these parameters, the performance of the Classification Model 440 can be varied in terms of sensitivity and specificity when these labels are compared to ground truth. These tunable parameters enable the Eye Disease analyzer phase 400 to be useful in different clinical applications. For example, high sensitivity can be used to increase the number of cases with detectable disease. On the other hand, high specificity can be used to decrease the number of false positive images and increase the efficiency of the Eye Disease analyzer phase 400 when compared to human-based labeling of images or groups of images.

In another embodiment of the present invention a Two-tier Threshold phase comprises a method to assign labels to images in two steps. The first step comprises a Classification Model 440 tuned for high sensitivity, for example approximately 90%, which maximizes detection of true positive images. These images are then processed by a second Classification Model 440 that is tuned for high specificity, for example approximately 90%, which minimizes false positive images. Images that are assessed as including signs of detectable disease by both versions of the Classification Model 440 are preferably assigned the label of "Refer to specialist", since they include the highest risk of including signs of threatening disease. The images assessed as including signs of detectable disease by the high sensitivity model but not the high specificity model are preferably assigned the label "Refer" which indicates that a non-specialist may be appropriate to follow up with the patient. It will be known to those skilled in the art that there are various ways of using and combining one or more alternative implementations of an Eye Disease analyzer 400.

In one embodiment of the present invention, computer systems and communication infrastructure are composed of frame buffer (not shown) to the display monitor. Computing Unit 600 preferably includes a main memory, for example random access memory ("RAM"), read-only memory ("ROM"), mass storage device, including an automated onsite and off-site backup system. Computing Unit 600 may also include a secondary memory such as a hard disk drive, a removable storage drive, an interface, or any combination thereof. Computing Unit 600 may also include a communications interface, for example, a modem, a network interface (such as an Ethernet card), a communications port, a PCM-CIA slot and card, wired or wireless systems, or other means of electronic communication. Computer programs are preferably stored in main memory and/or secondary memory. Computer programs may also be received via communications interface. Computer programs, when executed, enable the computer system, particularly the processor, to implement the methods according to the present invention. The methods according to embodiments of the present invention may be implemented using software stored in a computer program product and loaded into the computer system using removable storage drive, hard drive or communications interface. The software and/or computer system described herein may perform any one of, or any combination of, the steps of any of the methods presented herein. It is also contemplated that methods according to embodiments of the present invention may be performed automatically, or may be invoked by some form of manual intervention.

Embodiments of the present invention are also directed to computer products, otherwise referred to as computer program products, to provide software to the computer system. Computer products store software on any computer useable medium. Such software, when executed, implements the methods according to one embodiment of the present invention. Embodiments of the present invention employ any computer useable medium, known now or in the future. Examples of computer useable mediums include, but are not limited to, primary storage devices (e.g., any type of random access memory), secondary storage devices (e.g., hard drives, floppy disks, CD ROMS, tapes, magnetic storage devices, optical storage devices, Micro-Electro-Mechanical Systems ("MEMS"), nanotechnological storage devices, cloud storage, etc.), and communication mediums (e.g., wired and wireless communications networks, local area networks, wide area networks, intranets, etc.). It is to be appreciated that the embodiments described herein can be implemented using software, hardware, firmware, or combinations thereof. The computer system, or network architecture, of FIG. 3 is provided only for purposes of illustration, such that the present invention is not limited to this specific embodiment. It is appreciated that a person skilled in the relevant art knows how to program and implement the invention using any computer system or network architecture.

Image Quality Analyzer phase 300 and Eye Disease analyzer phase 400 preferably use machine-coded mathematical algorithms running in a Computing Unit 600. An embodiment of Computing Unit 600 preferably comprises a self-contained unit comprising one or more human-machine interfaces, power supplies, memories, processing units, and storage units and is preferably connected directly to the Retinal Camera 200 through a communication medium that transports the live video feed 270. Further, a Computing Unit 600 is preferably integrated into the base of the Retinal Camera 200 such that said Computing Unit 600 does not add to the footprint and space requirements of the Retinal Camera 200. It will be known to those skilled in the art that there are alternatives to the Computing Unit 600 and that all said alternatives perform the same function as the Computing Unit 600 described herein.

Figure 28:
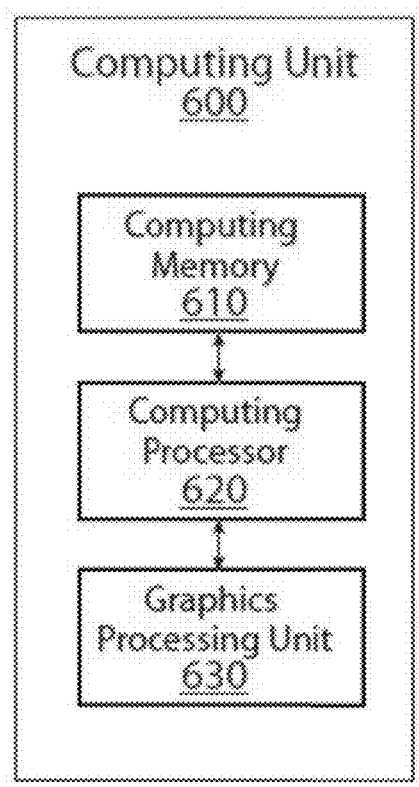
FIG. 28 depicts elements in a computing unit 600.

An embodiment of Computing Unit 600 comprises one or more machine-implemented tools and applications to distribute, manage, and process retinal images transmitted by the retinal camera 200. The Computing Unit 600 further comprises one or more types of computing memory 610, computing processors 620, and graphic processing units 630. FIG. 28 illustrates an embodiment of computing unit 600. The computing memory 610 preferably comprises solid state and magnetic memory media to store the image data to be processed as well as data generated during intermediate steps in the Image Quality Analyzer phase 300 and the Eye Disease analyzer phase 400. The computing processors 620 preferably execute machine-coded algorithms on solid state computer circuits according to the Image Quality Analyzer phase 300 and the Eye Disease analyzer phase 400. One or more graphic processing units 630 preferably comprise two or more parallelized solid state computing cores to divide processing tasks into pieces that can be done in parallel in said computing cores.

Figure 29:
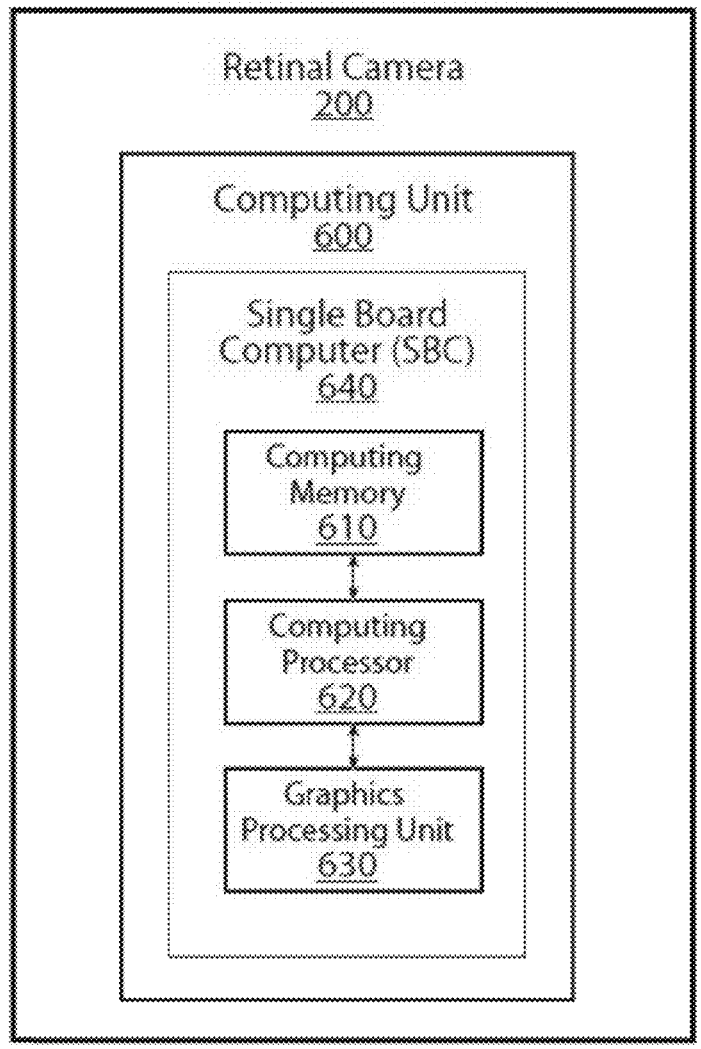
FIG. 29 depicts computing unit processing 600 using a single board computer (SBC) 640.
Figure 30:
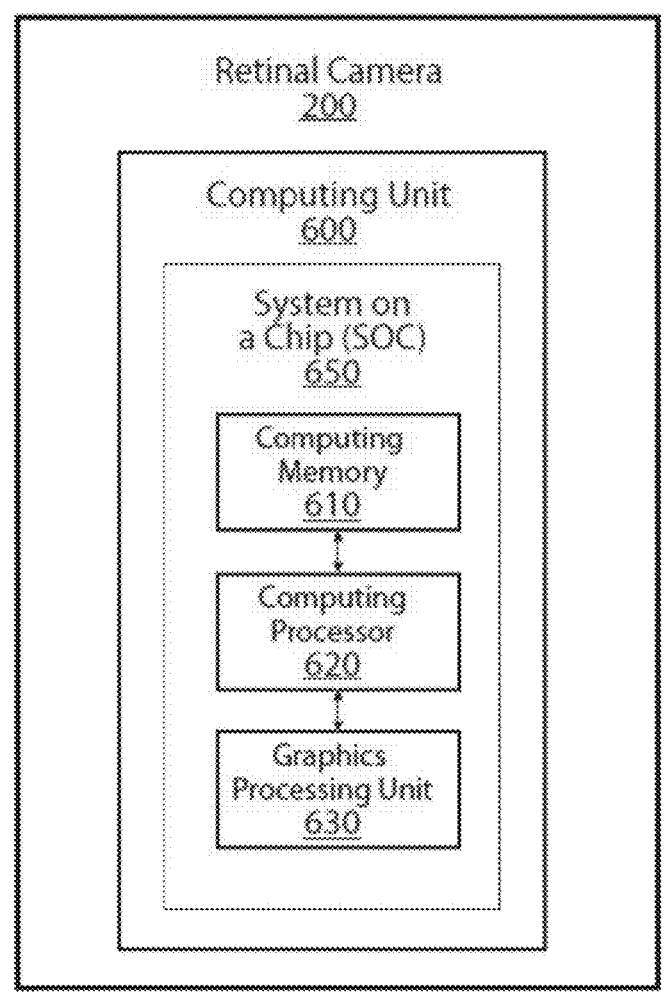
FIG. 30 depicts computing unit processing 600 using a system on a chip (SOC) 650.
Figure 31:
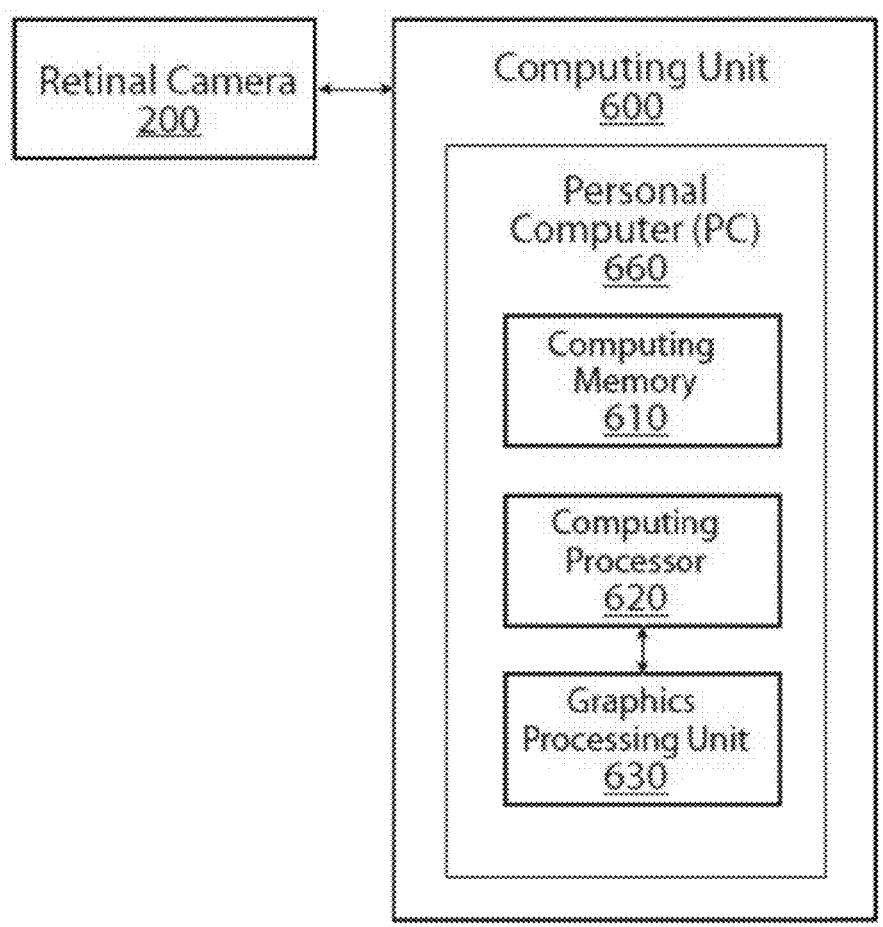
FIG. 31 depicts computing unit processing 600 using a personal computer (PC) 660.
Figure 32:
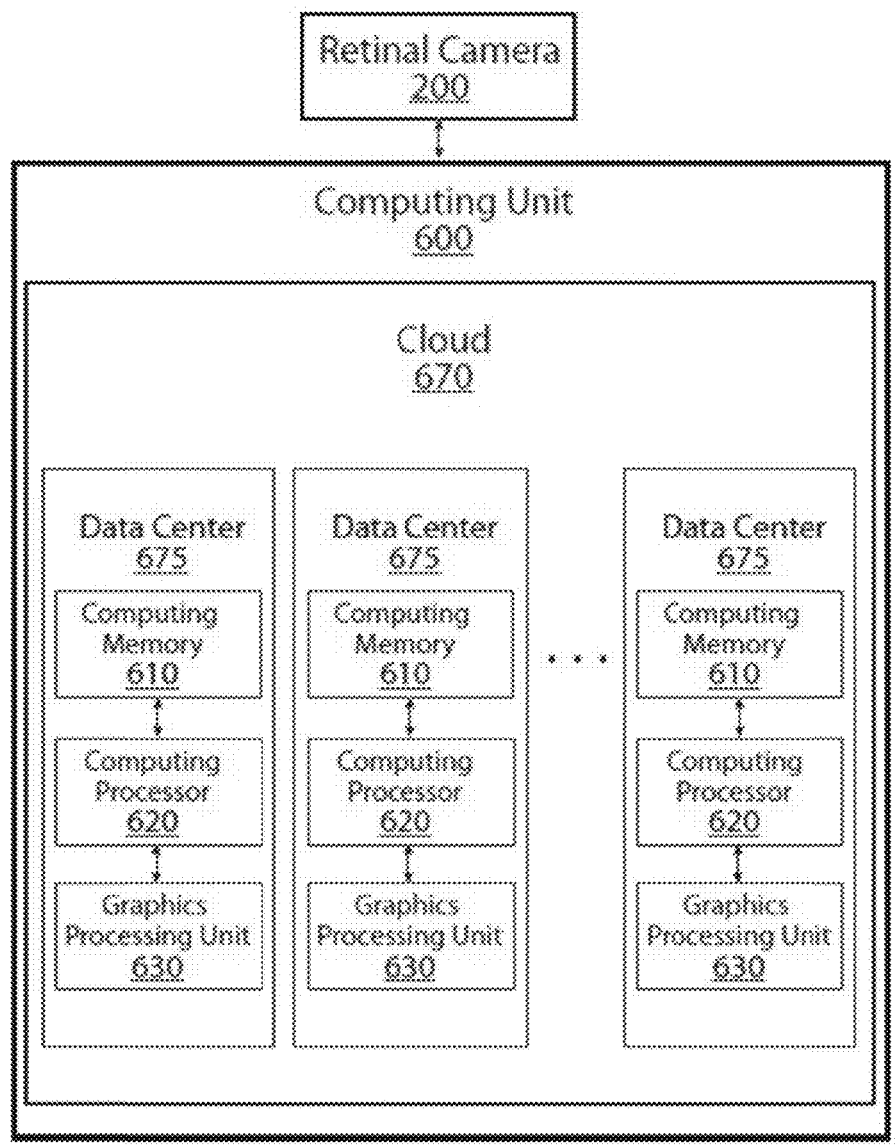
FIG. 32 depicts computing unit processing 600 using cloud computing 670.
Figure 33:
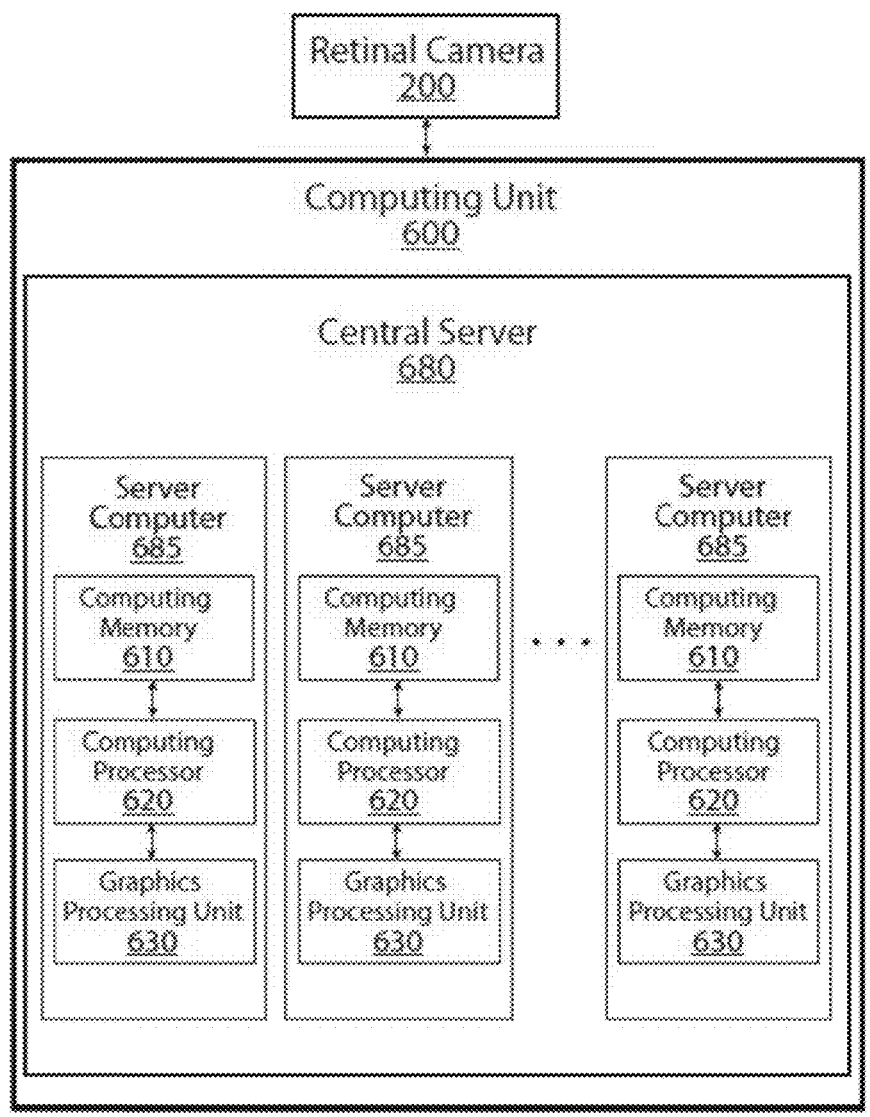
FIG. 33 depicts computing unit processing 600 using a central server 680.

FIG. 29 illustrates an embodiment of the present invention comprising a Computing Unit 600 comprising computing memory 610, computing processors 620, and graphic processing units 630 implemented as a single board computer (SBC) 640 that can operate onboard the retinal camera 200. FIG. 30 illustrates an embodiment of the present invention comprising a Computing Unit 600 comprising computing memory 610, computing processors 620, and graphic processing units 630 implemented as a system on a chip (SOC) 650 that can be located onboard the retinal camera 200. FIG. 31 illustrates an embodiment of the present invention comprising a Computing Unit 600 comprising computing memory 610, computing processors 620, and graphic processing units 630 implemented in a personal computer (PC) 660 that can operate separate and independently from the retinal camera 200. FIG. 32 illustrates an embodiment of the present invention comprising a Computing Unit 600 comprising computing memory 610, computing processors 620, and graphic processing units 630 implemented as a cloud based system 670 through an Internet connection to a distributed data center 675 and operated separately and independently from the retinal camera 200. FIG. 33 illustrates an embodiment of the present invention comprising a Computing Unit 600 comprising computing memory 610, computing processors 620, and graphic processing units 630 implemented as a centralized processing center or central server 680 through a wired, wireless, or internet connection to one or more dedicated server computers 685 and operated separately and independently from the retinal camera 200. It will be known to those skilled in the art that there are various alternatives to implement a Computing Unit 600 and that these alternatives perform the same function as the Computing Unit 600 described herein.

It will be understood that the embodiments disclosed and defined in the specification herein extend to all alternative combinations of the individual features mentioned or evident from the text or drawings. All of these different combinations constitute various alternative aspects of the embodiments of the present invention. Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all patents and publications cited above are hereby incorporated by reference.

What is claimed is:

1. A method to perform automatic retinal screening, the method comprising the steps of:
    illuminating a retina using an illumination source;
    capturing a digital retinal image with a retinal camera supported by a platform;
    transmitting the digital retinal image to a processor;
    performing via the processor an assessment in real time of the image quality wherein image quality is determined by one or more of the image quality steps of:
        determining a position of the Optical Disc or Macula relative to the digital retinal image obtained;
        determining percent of total pixels obscured by shadowing; and
        determining the value of the third quartile of a histogram of a gradient of pixel values from the digital retinal image;
    adjusting the digital retinal camera if the image quality does not meet predetermined image quality requirements; and
    executing real time analysis of presence or absence of disease in the digital retinal image
        wherein the digital retinal image is inadequate to meet the predetermined image quality requirement when one or more of the following is present: i) the number of pixels in the third quartile of a gradient image of the digital retinal image occupies more than 15 percent of the image area, ii) the total number of pixels within 10 percent of saturation is larger than 25 percent of the total number of pixels in the image after inverting values of a thresholded image, iii) a macula position is at an angle greater than between 0 degree and 20 degrees below a position of an optic disc with respect to a horizontal axis of the digital retinal image, iv) a distance between an optic disc center and a macula is more than two optic disc diameters and less than three optic disc diameters, v) an optic disc and a macula are positioned within one-third and two-thirds sections of a vertical digital image, and vi) a macula is positioned within a vertical region limited by temporal vessel arcades.

2. The method of claim 1 wherein the performing step determines alignment of the image according to one or more imaging protocols.

3. The method of claim 2 additionally comprising assigning a descriptive label to the image as to its adequacy according to one or more imaging protocols.

4. The method of claim 1 wherein the performing step determines presence and extent of crescents and shadows in the image.

5. The method of claim 4 additionally comprising assigning a descriptive label to the image as to presence and extent of crescents and shadows.

6. The method of claim 1 wherein the performing step determines quantitative image quality of the image via a classification process trained using examples of visual perception by human experts.

7. The method of claim 6 additionally comprising assigning a descriptive label to the image as to its quantitative image quality.

8. The method of claim 1 wherein the performing step classifies the image according to a set of image quality labels.

9. The method of claim 8 additionally comprising assigning a descriptive label to the image as to its image quality.

10. The method of claim 1 wherein the adjusting step employs a user interface to indicate a user quality of the image and suggested actions to take with respect to the camera.

11. The method of claim 1 additionally comprising assigning a label to the image indicative of the likelihood.

12. The method of claim 1 wherein the executing step employs a decomposition phase using AM-FM methods to decompose the image into magnitude, frequency, and angle of each image pixel across a plurality of spatial scales.

13. The method of claim 12 wherein the executing step additionally employs a feature extraction phase to group decomposition phase components into feature vectors.

14. The method of claim 13 wherein the executing step additionally employs a feature reduction phase to reduce number of features.

15. The method of claim 1 wherein the executing step additionally comprises tuning one or more parameters to vary assignment of labels and/or performance of a classification model in terms of sensitivity and specificity.

16. The method of claim 15 wherein the executing step employs a two-tier threshold to assign labels to the image in two steps.

17. The method of claim 16 where the first step comprises a high sensitivity classification model.

18. The method of claim 17 where the second stop comprises a high specificity classification model.

19. A system to perform automatic retinal screening, said system comprising:
   an illumination source illuminating a retina;
   a retinal camera capturing a retinal image wherein the retinal camera is supported by a platform;
   a processor receiving the image and performing an assessment in real time of the image quality; and
   adjusting a setting of the camera if the image quality does not meet predetermined quality requirements.

20. A method to automatically determine image quality of a digital retinal image, the method comprising the steps of:
   illuminating a retina using an illumination source;
   capturing the digital retinal image with a retinal camera supported by a platform;
   transmitting the image to a processor;
   performing via the processor an assessment in real time of the image quality, comprising:
   determining alignment of the image according to one or more imaging protocols;
   determining presence and extent of crescents and shadows in the image;
   determining quantitative image quality of the image via a classification process trained using examples of visual perception by human experts; and
   adjusting the camera if the image quality does not meet a predetermined quality requirement.

21. The method of claim 20 wherein the digital retinal image is inadequate to meet the predetermined image quality requirement for shadowing when a number of pixels in a third quartile of a gradient image of the digital retinal image occupies more than 15 percent of an image area of the digital retinal image.

22. The method of claim 20 wherein the digital retinal image is inadequate to meet the predetermined image quality requirement for crescents when a total number of pixels within 10 percent of saturation is larger than 25 percent of a total number of pixels in the digital retinal image after inverting values of a thresholded image.

23. The method of claim 20 wherein the digital retinal image is inadequate to meet the predetermined image quality requirement for alignment when a macula position is at an angle greater than between 0 degree and 20 degrees below a position of an optic disc with respect to a horizontal axis of the digital retinal image.

24. The method of claim 20 wherein the digital retinal image meets the predetermined image quality requirement for alignment when a distance between an optic disc center and a macula is more than two optic disc diameters and less than three optic disc diameters.

25. The method of claim 20 wherein the digital retinal image meets the predetermined image quality requirement for alignment when an optic disc and a macula are positioned within one-third and two-thirds sections of a vertical digital image.

26. The method of claim 20 wherein the digital retinal image is adequate to meet the predetermined image quality requirement when a macula is positioned within a vertical region limited by temporal vessel arcades.

* * * * *